(12) United States Patent
Sevick-Muraca et al.

(10) Patent No.: US 6,930,777 B1
(45) Date of Patent: Aug. 16, 2005

(54) METHOD FOR CHARACTERIZING PARTICLES IN SUSPENSION FROM FREQUENCY DOMAIN PHOTON MIGRATION MEASUREMENTS

(75) Inventors: Eva M. Sevick-Muraca, College Station, TX (US); Zhigang Sun, Houston, TX (US); Yingqing Huang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 525 days.

(21) Appl. No.: 10/115,271

(22) Filed: Apr. 3, 2002

Related U.S. Application Data
(60) Provisional application No. 60/281,102, filed on Apr. 3, 2001, and provisional application No. 60/333,160, filed on Nov. 19, 2001.

(51) Int. Cl.[7] .............................................. G01N 15/02
(52) U.S. Cl. ...................................................... 356/336
(58) Field of Search ................................ 356/336, 337, 356/338, 342; 702/29, 129, 156

(56) References Cited

U.S. PATENT DOCUMENTS

| | | | |
|---|---|---|---|
| 5,818,583 A | * | 10/1998 | Sevick-Muraca et al. ... 356/336 |
| 5,865,754 A | | 2/1999 | Sevick-Muraca et al. ... 600/476 |

FOREIGN PATENT DOCUMENTS

| | | | | |
|---|---|---|---|---|
| EP | 0 959 341 A1 | 11/1999 | | |
| GB | 2311366 A | 3/1996 | .......... | G01N/21/49 |
| WO | WO 00/22414 | 8/1999 | .......... | G01N/21/00 |

OTHER PUBLICATIONS

Sun, et al., *"Particle Characterization of Colloidal Suspension at High Volume Fractions Using Frequencey Domain Photon Migration"*, 6th World Congress of Chemical Engineering Melbourne 2001, pp. 4/15–12/15, 2001.

Sun, et al., *"Inversion Algorithms for Particle Sizing with Photon Migration Measurement"*, Fluid Mechanics and Transport Phenomena, AIChE Journal, vol. 47, No. 7, pp. 1487–1498, Jul. 2001.

Sun, et al., *"Approach for Particle Sizing in Dense Polydisperse Colloidal Suspension Using Multiple Scattered Light"*, XP–001126299, Langmuir 2001, 17, 2000 American Chemical Society, pp. 6142–6147, Sep. 8, 2001.

(Continued)

*Primary Examiner*—Gregory J. Toatley, Jr.
*Assistant Examiner*—Roy M. Punnoose
(74) *Attorney, Agent, or Firm*—Baker Botts L.L.P.

(57) ABSTRACT

Methods are provided for measuring isotropic scattering coefficients of suspensions using multiply scattered radiation that is modulated in amplitude at selected modulation frequencies. The radiation may be light. Quantities describing diffusion of the multiply scattered radiation are preferably measured at a plurality of distances between source and receiver and a plurality of frequencies. Linear regression techniques are provided for maximizing accuracy of the scattering data at a selected wavelength of a radiation. Methods are provided for inversing an integral equation so as to determine a calculated value of scattering coefficient. Parameters are varied to minimize the difference between the calculated and measured scattering coefficients and thereby to determine volume fraction, particle size distribution and interparticle force between the particles in a suspension. By incorporating a first principles model to account for interparticle force, the measurements can be used to determine a parameter governing interparticle forces in a suspension. The suspension may be in a liquid or a gas.

19 Claims, 19 Drawing Sheets

OTHER PUBLICATIONS

PCT Invitation to Pay Additional Fees (PCT Article 17(3)(a) and Rule 40.1), Annex to Form PCT/ISA/206 Commucation Relating to the Results of the Partial International Search, from the International Searching Authority, regarding PCT/US 02/ 10433 filed Mar. 4, 2002, Applicant's reference 017575.0748, 6 pages, Nov. 29, 2002.

Richter, et al., "Particle Sizing Using Frequency Domain Photon Migration", Particle and Particle Sustems Characterization vol. 15, No. 9, Feb. 1998, XP008010433, pp. 9–15.

Isayev, K. et al., "Study of Thermophysical Properties of a Metal–Hydrogen System", International Journal of Hydrogen Energy, vol. 21, No. 11–12, Nov. 12, 1996, pp 1129–1132.

Panda, et al., "Generalized B–spline Signal Processing", European Journal Devoted to the Methods and Applications of Signal Processing, Elsevier Science Publishers, B.V. Amsterdam, NL, vol. 55, No. 1, Nov. 1, 1996 XP004016005, pp. 1–14.

PCT Search Report, PCT/US 02/10433, Jun. 16, 2003.

* cited by examiner

METHOD FOR CHARACTERIZING PARTICLES IN SUSPENSION FROM FREQUENCY DOMAIN PHOTON MIGRATION MEASUREMENTS

This application claims the benefit of Provisional Patent Application No. 60/281,102, filed Apr. 3, 2001, and claims benefit of Provisional Patent Application No. 60/333,160, filed Nov. 19, 2001.

GOVERNMENT RIGHTS IN THE INVENTION

The U.S. government has a paid-up license in this invention and the right in limited circumstances to require the patent owner to license others on reasonable terms as provided for by the terms of Grant No. CTS-9876583, awarded by the National Science Foundation.

BACKGROUND OF THE INVENTION

1. Field of the Invention

This invention relates to measurements of particle characteristics using multiply scattered radiation. More particularly, methods for obtaining more precise Frequency Domain Photon Migration (FDPM) data and obtaining from the data particle size distributions, volume fractions, and interparticle force characteristics for interacting particles and polydisperse or multi-modal size distributions are provided.

2. Discussion of Related Art

On-line measurements of particle size distribution and volume fraction of colloidal suspensions are needed in various processes of chemical and other industries. The measurements may be used, for example, to evaluate, optimize, and control manufacturing processes or to control product quality.

On-line particle-sizing methods such as turbidity, angular static light scattering and dynamic light scattering, based on light scattering from a single particle, are often used. These methods require considerable dilution of most commercial suspensions to avoid the effects of multiple scattering and particle interaction. Dilution may alter the size distribution of the particles. Otherwise used without dilution, empirical calibration of the instruments with like-suspensions of particles to be sized is necessary. Methods have been proposed to suppress the effects of multiple scattering, such as fiber optic dynamic light scattering (FODLS) and modified static light scattering, but these methods are not well suited for particle sizing of multiple scattering, dense colloidal suspensions.

Recently, new optical particle sizing methods, such as Diffusing Wave Spectroscopy (DWS) and diffuse reflectance and/or transmittance spectroscopy have been used for dense colloidal suspensions. To provide accurate sizing information these methods require accounting for particle interactions at high volume fractions.

In recent years, alternatives to optical sizing methods have been developed. These include acoustic and electroacoustic spectroscopy. Similarly to light scattering methods, the acoustic and electroacoustic theories for dilute systems are relatively complete, but the theories for polydisperse concentrated systems are far from complete. While several models based on first principles have been developed to account for particle interactions in concentrated suspensions, few of the models have been successfully used in practical applications. Also, these acoustic methods require knowledge of the physical properties of each phase and electroacoustic spectroscopy can only be used for charged particles. Better methods for characterizing dense suspensions are needed. Further background information on these methods can be found in the article "Approach for Particle Sizing in Dense Polydisperse Colloidal Suspension Using Multiple Scattered Light," *Langmuir* 2001, 17, 6142–6147, which is hereby incorporated by reference herein.

Frequency Domain Photon Migration (FDPM) has been proposed for particle measurements (U.S. Pat. No. 5,818,583, for example). Since this technique measures time-dependent propagation characteristics rather than the amount of light detected, it has the major advantage of not requiring calibration. In addition, FDPM measurements allow determination of absorption and scattering properties independently. Therefore, FDPM allows characterizations of colloidal suspension by scattering measurements that are not biased by changes in light absorption or color of suspending fluids. Because FDPM depends on multiply scattered light, it is restricted to particulate suspensions that are concentrated enough to cause multiple scattering events as radiation is transmitted through the suspension. Such suspensions are typically opaque. Using the FDPM method, both size distribution and volume fraction can be directly obtained by inversion algorithms, where the only physical parameter required a priori is the relative refractive index between the particulate and continuous phases. Since no dilution is necessary to avoid multiple scattering, FDPM is suitable for online monitoring of particle size distribution and volume fraction in many commercial processes that include particles or droplets. FDPM has been successfuiily used for recovery of particle size distribution and volume fraction in opaque, multiple scattering suspensions of polystyrene and of titanium dioxide, for example (S. M. Richter et al., "Particle Sizing Using Frequency Domain Photon Migration," *Part. Part. Syst. Charact.*, 15, 9, 1998).

Using visible wavelengths, particles from 50 nm to greater than 1 micron in diameter may be characenized in multiple scattering, non-interacting suspensions. However, at volume fractions larger than about 1–5%, corrections for particle interaction become increasingly necessary. Particle interactions can arise from volume exclusion effects as well as from particle interactions, which arise owing to forces that act between particles. As a results of these interactions, the particle suspension becomes ordered and structured. This order and structure impacts scattering and must not only be used to perform sizing, but when sizing information is available, can be used to determine the nature of particle interactions, (S. M. Richter et al, "Characterization of Concentrated Colloidal Suspensions Using Time Dependent Photon Migration Measurements," *Colloid Surf. A*, 172, 163, 2000).

Determination of particle characteristics from FDPM data requires solving mathematically an "ill-posed" inverse problem. Error in the FDPM data used to solve the inversion equations has a large effect on particle size distribution, particle size, and other calculated results. Therefore, there is a need for apparatus and method for determining the FDPM (scattering) data to a high degree of accuracy. Further, a method for indicating the quality of the data is needed, such as with a quality parameter that indicates whether the measurement is precise enough for use in an inverse solution. In application Ser. No. 09/297,895, which is hereby incorporated by reference, measurements at multiple modulation frequencies and two locations were disclosed. Since results are non-linear at multiple frequencies, a non-linear regression method of analysis was necessary. A linear method of analysis and method for treating results of measurements from multiple measurements for maximum accuracy are needed.

In previous work on FDPM, particle size distributions were assumed to be either normal, log-normal or Weibull distributions. A method for determining an unknown and arbitrary particle size distribution is needed for polydisperse and multi-modal suspensions, at non-interacting or interacting (high) volume fractions.

Many suspensions of commercial interest contain volume concentrations of the disperse phase far above the 1–5 per cent by volume range, where particles can be considered non-interacting. In addition to the methods for determining volume fraction and particle size distribution when particle interaction must be considered, methods for indicating any attractive or repulsive forces between the interacting particles are needed, since such forces are important in determining stability, Theological properties, and other properties of the high-volume-fraction suspensions. These interparticle forces, along with the volume exclusion effects, cause additional order within the suspension. Therefore, methods for interpreting interparticle forces as result of the order are needed. In applying FDPM to a particular sample containing particles, various models may be used to interpret a measured scattering coefficient in terms of particle concentration, particle size distribution and inter-particle forces. In the method disclosed in Ser. No. 09/297,895, interparticle interactions arising from volume exclusion were interpreted assuming a monodisperse sample. Methods for considering more general particle size distributions are needed. A device that includes a processor to execute computer programs to provide results in terms of the various models is needed.

SUMMARY OF THE INVENTION

Method for measuring isotropic scattering coefficient for multiply scattered radiation passing through a suspension is provided. In one embodiment, the radiation is modulated at a selected frequency and measurements selected from among AC attenuation, DC attenuation and phase change of the radiation are made at different distances apart of a source and a detector of the radiation. In another embodiment, the measurements are repeated at different modulation frequencies. The measurements may be used in linear equations to calculate absorption and scattering coefficient of the radiation. Simultaneous regression of combinations of the characteristics of the radiation is provided. A "criteria parameter" is provided for determining the experimental quality of the measurements.

Method for determining volume fraction, particle size distribution and interparticle force is provided. Differences between experimental values of scattering coefficient at selected wavelengths of radiation and calculated values of scattering coefficient at the same selected wavelengths are minimized using a least squares minimization. The inversing of an integral equation describing calculated values of scattering coefficient may be stabilized using Tikhonov regularization and a non-negativity constraint. Particle size distribution and volume fraction are separated by a normalized distribution constraint. Determination of particle size distribution is not limited to a priori assumptions. Monodisperse and polydisperse suspensions, either single- or bi-modal may be investigated using the methods disclosed herein.

The Hard Sphere model of particle interaction is applied, along with modifications of this model. Models accounting for interparticle forces are developed, including the inclusion of a first principles model of particle interaction, which makes possible investigation of interparticle forces that are important in determining rheology, stability and other properties of colloidal suspensions.

Apparatus is provided for measuring scattering coefficients that includes a source or multiple sources and a receiver or multiple receivers at multiple distances apart in a sample of suspension. In one embodiment, a source or detector is mechanically moved to allow measurements are multiple distances apart of the source and detector. A system for executing a computer program to perform the calculations is also provided.

DESCRIPTION OF PREFERRED EMBODIMENTS

Figure 1A:
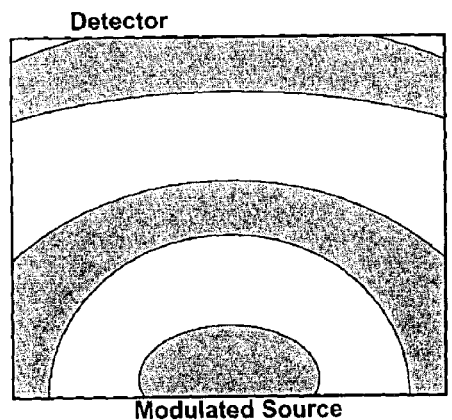
FIG. 1(a) depicts a radiating wave of varying intensity propagating through a scattering medium and FIG. 1(b) illustrates source and detected waves along with measurements used in FDPM measurements.
Figure 1B:
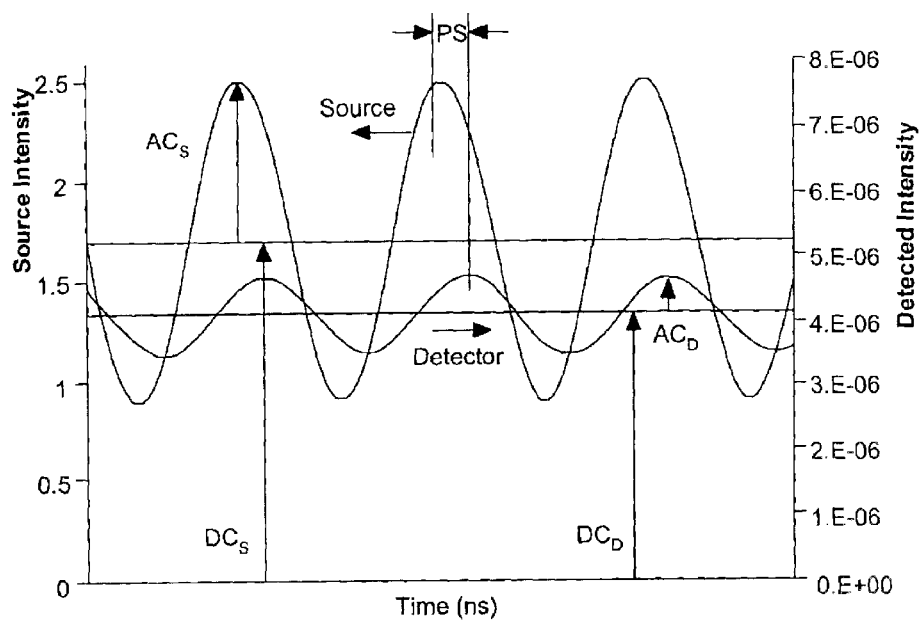

FIG. 1(a) depicts variations of light intensity in a scattering medium between a modulated source and a detector. Frequency Domain Photon Migration (FDPM) measurements involve the time-dependent propagation characteristics of multiply scattered light having a selected wavelength in the scattering medium. U.S. Pat. No. 5,818,583 and PCT application WO 98/20323, which are incorporated by reference herein, disclose apparatus and methods for making and interpreting FDPM measurements for the purposes of characterization of particles. The technique depends on introducing intensity-modulated light into a multiply scattering medium at a point source and detecting transmitted light at one or more discrete points removed from the source. FIG. 1(b) illustrates quantities that are measured in obtaining FDPM data. Phase shift (PS) between the source and detected signal, the amplitude of the alternating signal of the modulation at the source ($AC_s$) and at the detector ($AC_d$) and the time-average signal at the source (DCs) and at the detector ($DC_d$) may be measured. Measurements of these quantities are used as described below to calculate properties of a scattering sample between the source and detected signal.

Figure 2A:
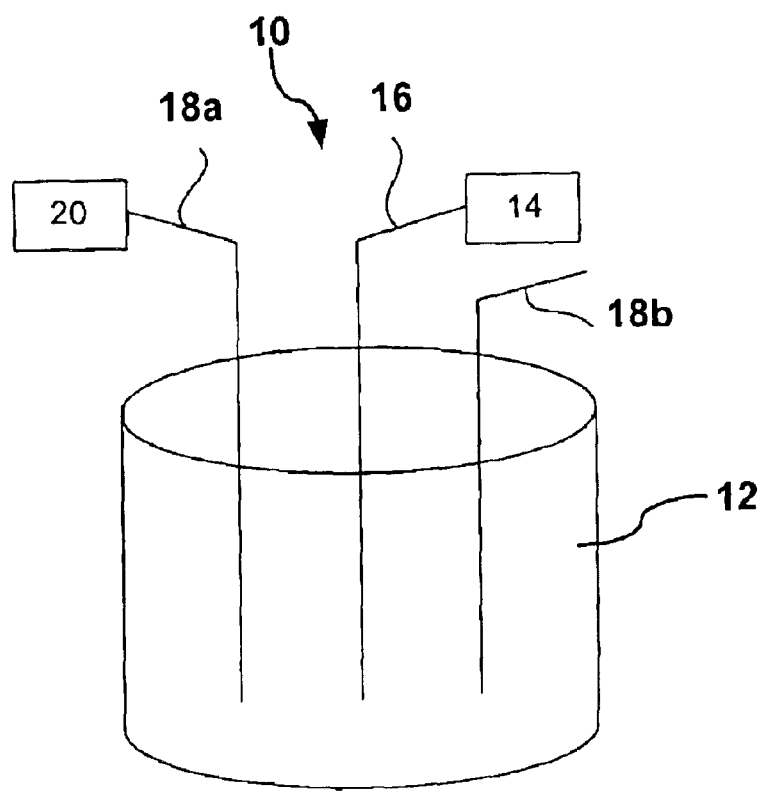
FIG. 2(a) shows an isometric view and FIG. 2(b) a plan view of one embodiment of apparatus for FDPM measurements.
Figure 2B:
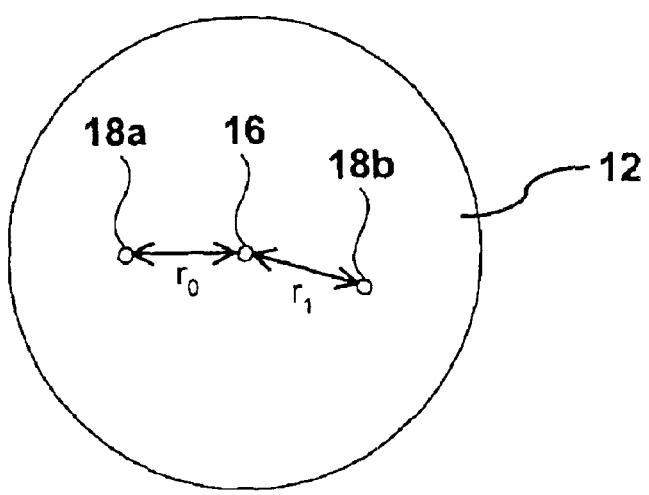

FIG. 2 illustrates one embodiment of apparatus 10 that may be used for FDPM measurements. Experimental conditions preferably provide in effect an infte scattering medium around a source of radiation, although other geometries are possible. This may be achieved by placing a fiber optic source of radiation and fiber optic receiver probes in a sample container. The container may have a volume of 100 mL, for example. Alternatively, one or more sources of radiation may be placed directly in the sample and one or more detectors may also be placed directly in the sample. The source may be a laser, an LED, or other source that can be modulated in intensity in the frequency range where measurements are to be made. Preferably, a laser diode is used. The source may be interchangeable or adjustable, or be comprised of an array to produce a plurality of selected wavelengths of light. The source and one or more receiver fibers may be placed at fixed distances apart or the relative separations between the source and detector fibers may be adjusted mechanically. Distances between source and detector fibers should be at least ten isotropic scattering mean free paths, to satisfy conditions of multiple light scattering. Preferably, distances between the source and receiver fibers are measured to an accuracy of at least about 0.1 per cent.

Referring to FIG. 2, radiation source 14 provides modulated radiation into source fiber 16, which ends in sample container 12. First receiver fiber 18(a), preferably ending in the same plane as the first fiber and at a spaced-apart distance, $r_o$, in that plane is used to detect a signal propagating through the sample and to convey the signal to photodetector 20. Second receiver optical fiber 8(b) may be placed at a second spaced-apart distance, $r_1$, from source fiber 16. Additional receiver optical fibers 18(c, d, . . . ) may be placed at selected spaced-apart distances from fiber 16, preferably in a pattern around fiber 16 so as to avoid placement of any fiber in the direct path of radiation to another fiber. Alternatively, fibers may be moved from a first distance, such as $r_o$, to a selected number of distances, r, from the source. In another embodiment, source fiber 16 may be moved to multiple locations for measurements at different source-receiver distances while receiver fibers remain stationary.

Figure 3:
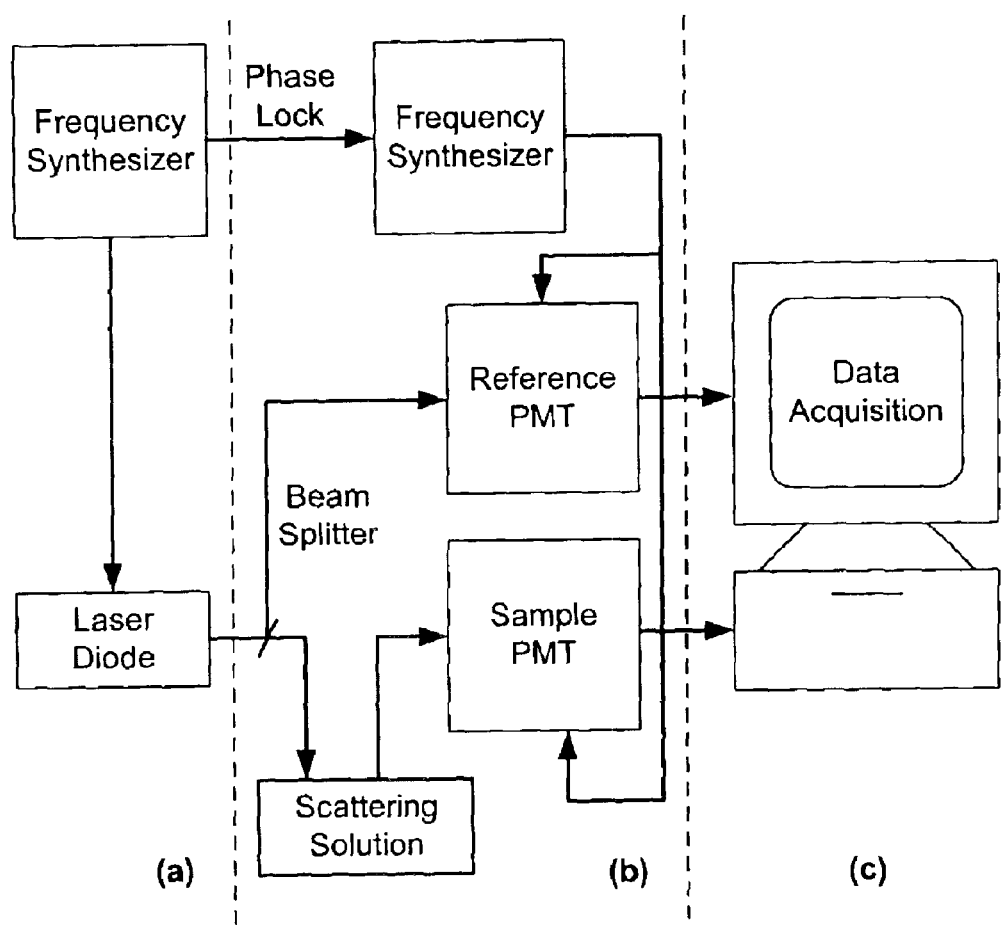
FIG. 3 shows a schematic of one embodiment of instrumentation that may be used in FDPM measurements.

Referring to FIG. 3, FDPM measurements may be performed with the electronic apparatus illustrated. FDPM instrumentation is made up of three major components: (a) the light source, (b) the light delivery and detection apparatus, and (c) the data acquisition and analysis system. A 687 nm or 828 nm wavelength laser diode (Thorlab, Inc., Newton, N.J.) may be used as a light source, for example. Other lasers, LEDs or other sources of radiation may be used. The output of the laser diode may be sinusoidally modulated at the frequencies of interest by a frequency synthesizer (Marconi Instruments signal Generator 2022A, Mountain View, Calif.). Common modulation frequencies are in the range from 10 MHz to 100 MHz. The modulated light from the laser source may be split by a glass beam-splitter so that approximately 10% of the light is collected by a reference Photo-Multiplier Tube (PMT) (Model H6573, Hamamatsu, Japan) via one 1000 µm optical fiber (FT-1.0-EMT, Thorlab, Inc., Newton, N.J.). The remaining transmitted light may be launched into the scattering solution (sample) using a second 1000 µm source optical fiber positioned vertically in the sample container. The scattered light from the sample may be detected by a third vertically positioned 1000 µm optical fiber and directed to the sample photo-detector (PMT). Both PMTs may be gain-modulated by an amplified RF signal from another frequency synthesizer (Marconi Instruments Signal Generator 2022A, Mountain View, Calif.) which is phase-locked to the first. A standard heterodyne technique may be employed to accurately process high frequency signals. Labview 5.0 software (National Instruments, Austin, Tex.) on a standard PC may be used as the platform for experimental data acquisition and analysis. More detailed description of the apparatus may be found in the paper "Precise Analysis of Frequency Domain Photon Migration Measurements for Characterization of Concentrated Colloidal Suspensions," by Sun, Z., Huang, Y. and E. M. Sevick-Muraca, *Rev. Sci. Instrum.*, 73(2): 383–393, 2002.

In concentrated particulate suspensions, the propagation of light can be modeled as a diffusion process, since photons are multiply scattered. The governing equation for the propagation of light through a multiple scattering medium in the diffusion approximation can be written as:

$$\frac{\partial U(r, t)}{\partial t} - vD\nabla^2 U(r, t) + v\mu_a U(r, t) = q_0(r, t) \quad (1)$$

where, U is the total photon density; $q_o$ is the isotropic source term; v is the speed of light in the medium; and D is the diffusion coefficient, which is defined as $$D = \frac{1}{3(\mu_a + \mu'_s)} \quad (2)$$

Herein, $\mu_a$ is the absorption coefficient and $\mu'_s$ is the isotropic scattering coefficient that arises from multiple scattering $$\mu'_s(\lambda) = (1-g)\mu_s(\lambda) \quad (3)$$

where $\mu_s$ is the scattering coefficient, and g is the average of the cosine of the scattering angle, or the scattering anisotropy. (A list of definitions of mathematical symbols used herein is provided at the end of this written description.)

In the case of a sinusoidally intensity-modulated point source of light and a uniform infinite medium boundary condition, Equation (1) (also called the photon diffusion equation) can be solved to yield analytical expressions for three experimentally determined quantities: (1) the steady-state photon density or the time invariant average intensity, termed the DC component; (2) the amplitude of the photon-density oscillation, termed the AC component; and (3) the phase shift of the photon-density wave, termed PS. FIG. 1(b) illustrates those quantities. The solution to Eq. (1), as flirther described in the paper "Approach for Particle Sizing in Dense Polydisperse Colloidal Suspension Using Multiple Scattered Light," Langmuir 2001, 17, 6142–6147, which provides an expression for the isotropic scattering coefficient for a polydisperse interacting colloidal suspension, which is:

$$\mu_s'(\lambda) = \int_0^\infty \frac{12\phi f(x)}{k^2 x^3} \left[ \int_0^\pi F(n, x, \lambda, \theta) S(q, \phi) \sin\theta (1 - \cos\theta) d\theta \right] dx \quad (4)$$

where $F(n,x,\lambda,\theta)$ is the form factor for a particle of diameter, x, with relative refractive index of particle to medium, n, at wavelength, $\lambda$, and $\theta$ is the scattering angle. The term $\phi$ represents the volume fraction of particles in the suspension and $f(x)$ represents Particle Size Distribution (PSD); k is given by $2 \pi m/\lambda$, where m is the refractive index of medium; q is the magnitude of the wave vector; $q=2 k \sin(\theta/2)$. In equation (4), the form factor, $F(n,x,\lambda,\theta)$, can be calculated by classical Mie scattering theory of single particle scattering, which is well known in the art. The structure factor, $S(q,\phi)$, is a direct measure of the local ordering of colloidal particles, and the value of $S(q,\phi)$ is equal to unity in the absence of particle interactions (e.g. in a dilute suspension).

For polydisperse systems, since particle interactions occur between colloids not only with the same particle size but also with different particle sizes, the partial structure factor, $S_{i,j}$, must be considered, where i and j represent particles with different sizes $x_i$ and $x_j$. Equation (4) becomes:

$$\mu_s'(\lambda) = \int_0^\pi \frac{12\phi}{k^2} \int_0^\infty \frac{f(x_i)}{x_i^3} \int_0^\infty \frac{f(x_j)}{x_j^3} F_{i,j}(n, x_i, x_j, \lambda, \theta) \cdot \quad (5)$$

$$S_{i,j}(n, x_i, x_j, \lambda, \theta) \sin\theta (1 - \cos\theta) dx_j dx_i d\theta$$

where $F_{i,j}$ is the binary form factor between the particles with different sizes $x_i$ and $x_j$.

If particle sizes are the same (i.e., i=j), the form factor is simply calculated as a monodisperse system:

$$F_{i,j} = (f_{1,i} f^*_{1,i} + f_{2,i} f^*_{2,i}) \quad (6)$$

where $f_{1,i}$ and $f_{2,i}$ are the scattering amplitudes into two orthogonal polarization states arising from a particle with size $x_i$, which can be calculated by Mie scattering theory. $f^*_{1,i}$ and $f^*_{2,i}$ are conjugates of $f_{1,i}$ and $f_{2,i}$ respectively. However, if particle sizes are different (i.e., i≠j), the binary form factor with different particle sizes is calculated by:

$$F_{i,j} = Re(f_{1,i} f^*_{1,j} + f_{2,i} f^*_{2,j}) \quad (7)$$

Referring to Eq. (5), since the scattering coefficient is a function of wavelength, $\lambda$, measurements of scattering coefficient at M different wavelengths provide a means for establishing a system of M equations that can be used to establish values for M parameters used to describe scattering in a suspension. If measurements are made at only one wavelength, the number of unknowns must be reduced to one by assumptions or other known conditions in the suspension. For example, if the volume concentration, $\phi$, is low enough to neglect interparticle forces, the structure factor, S, can be assumed to have a value of one. There are still two unknowns, $\phi$ and $f(x)$. If volume fraction, $\phi$, is known and it is known that the sample is monodisperse, then the single particle diameter can be determined with measurements at only one wavelength, $\lambda$. If the sample of known volume fraction is polydisperse but assumed to have a particle size distribution described as Gaussian or log-normal, which is described by two parameters, measurements at two wavelengths will be necessary and sufficient to determine the two parameters used to describe those distributions. If the particle size distribution is of unknown shape, even possibly bi-modal, more complex size distribution models are necessary, as will be described below and more measurements at different wavelengths will be necessary to describe the particle size distribution. If the volume fraction is not known, then measurements are required at an additional wavelength to determine the additional unknown parameter, $\phi$, in Eq. (5).

It should thus be clear that Eq. (5) can be used for two general types of investigations of suspensions: particle sizing and assessment of particle interactions. Methods are disclosed herein for particle sizing measurements when the form of the particle size distribution is known, which may be uni-modal or multi-modal, with or without particle interaction. Methods are also disclosed for determining an unknown particle size distribution, which may be uni-modal or multi-modal, with or without considering inter-particle interactions. These methods include the assumption that the inter-particle interactions can be adequately treated using a "hard sphere" model or modifications of that model to approximate the volume exclusion effects that predominantly impact the structure. To use Eq. (5) for assessment of particle interactions, unknown or known forms of particle size distribution may be used. An iteration parameter may be used to indicate repulsive or attractive interparticle forces on an empirical basis and without a specified particle interaction model.

To determine the most accurate particle sizing data and particle interaction assessment, accurate measurements of isotropic scattering coefficients at each wavelength must be available. A preferred method for determining isotropic scattering coefficient, $\mu_s'$, is as follows: (1) using a source emitting a selected wavelength of light in the range from about 100 nm to about 2000 nm, measure the phase shift and either the AC or DC value of radiation intensity at a series of differing distances from the source of light, preferably using a selected modulation frequency in the range from about 10 MHz to about 300 MHz. The number of differing distances is preferably at least three and is more preferably in the range from about 5 to 10. Measurements at different distances, called Multi-Distance (MD), are preferably repeated at a series of modulation frequencies, called Multi-Frequency (MF). Preferably at least about three modulation frequencies are used, such as 30, 60 and 90 MHz.

The following equations can conveniently be used to perform calculations from the measurements:

$$\ln\left(\frac{r}{r_0} DC_{rel}\right) = -(r - r_0)[3\mu_a(\mu_a + \mu_s')]^{1/2} \quad (8a)$$

$$\ln\left(\frac{r}{r_0} AC_{rel}\right) = -(r - r_0)\sqrt{3\mu_a(\mu_a + \mu_s')/2} \left[\sqrt{1 + \left(\frac{\omega}{v\mu_a}\right)^2} + 1\right]^{1/2} \quad (8b)$$

-continued $$\ln(Mod_{rel}) = \qquad (8c)$$

$$-(r-r_0)\sqrt{3\mu_a(\mu_a+\mu_s')/2}\left[\sqrt{2}-\left(\sqrt{1+\left(\frac{\omega}{v\mu_a}\right)^2}+1\right)^{1/2}\right]$$

$$(PS_{rel}) = (r-r_0)\sqrt{3\mu_a(\mu_a+\mu_s')/2}\left[\sqrt{1+\left(\frac{\omega}{v\mu_a}\right)^2}-1\right]^{1/2} \qquad (8d)$$

wher $AC_{rel}$ is the ratio of AC measured at r to that measured at $r_o$, $PS_{rel}$ is the difference in measured phase at r and $r_o$, and $DC_{rel}$ is the ratio of DC measured at r to that measured at $r_o$.

Using equations 8a–8d, the optical absorption and scattering properties of the medium, $\mu_a$ and $\mu'_s$, can be estimated from the relative measurement data at two or more source-detector distances. In addition, the following expression can be derived from the above equations $$\frac{\ln^2(rAC_{rel}/r_0) - PS_{rel}^2}{\ln^2(rDC_{rel}/r_0)} = Q = 1 \qquad (9)$$

Eq. 9 can be used to check whether FDPM measurements are consistent with the assumptions of the photon diffusion model. We term Q the "criteria parameter". Since equation (9) is independent of the optical proprieties $\mu_a$ and $\mu'_s$, the value of Q can be used to optimize measurement conditions even before extracting the isotropic scattering coefficient by different data analysis approaches. So, it provides a useful criterion to assess the accuracy and precision of FDPM measurements under different experimental conditions.

Figure 4:
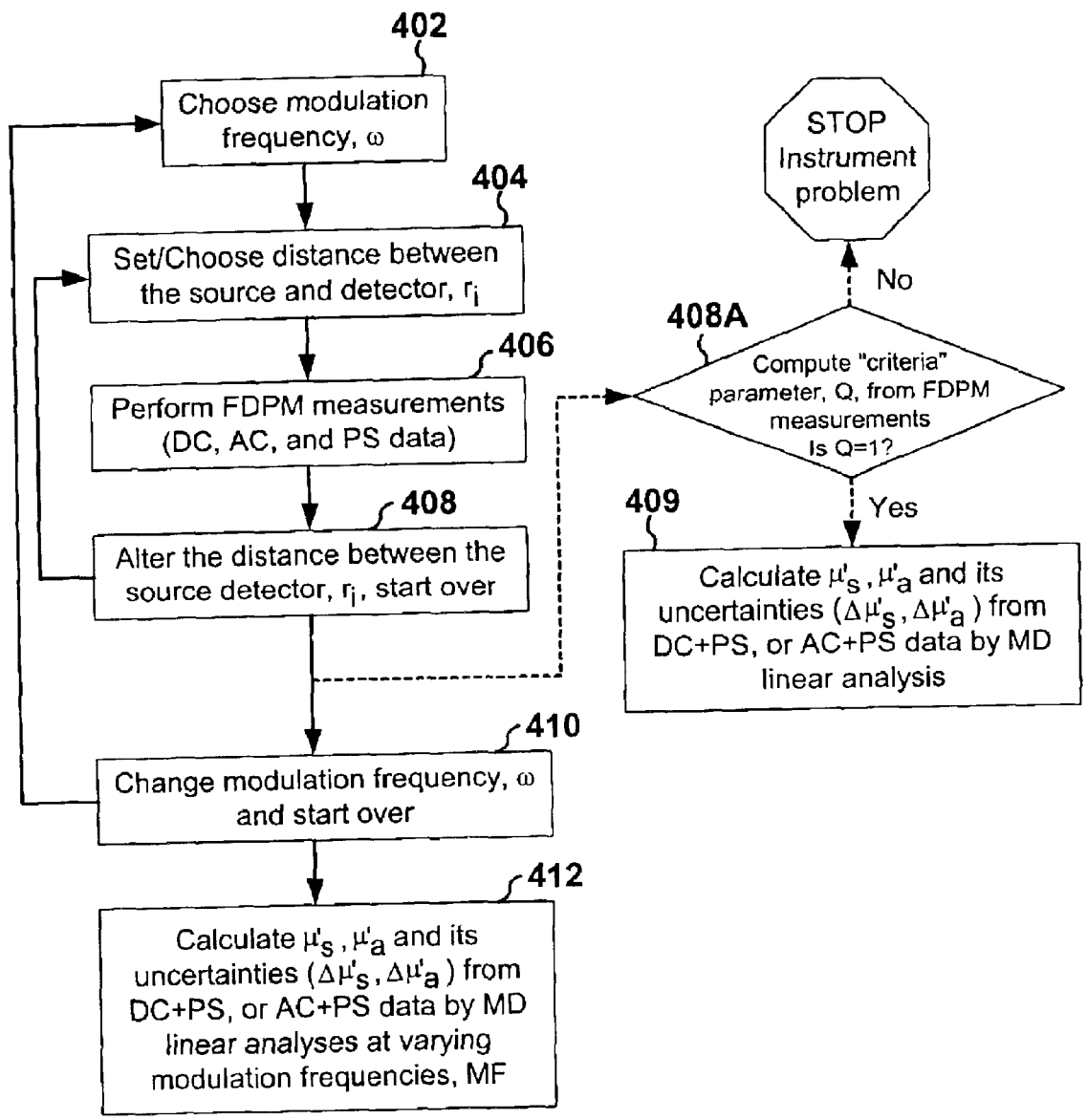
FIG. 4 illustrates a flowchart showing one embodiment of a method for determining scattering coefficients from FDPM measurements.

A flowchart describing a preferred procedure for determining $\mu'_s$ and $\mu_a$ from FDPM measurements as a selected wavelength of light is shown in FIG. 4. In step 402, a first modulation frequency is chosen, which is normally in the range of 10–300 MHz. In step 404, a first distance between the source and detector is chosen. In step 406, measurements of DC and AC intensity and phase shift are made at the first distance and frequency. In step 408, the distance is altered and measurements are repeated at the same modulation frequency. In step 408A, the criteria parameter, Q, is calculated. If Q has a value near 1, then scattering and absorption coefficients are calculated from the measurements and a linear analysis of the measurements at different distances. Measurements are then repeated at a different modulation frequency in step 410. In step 412, calculations are performed for the different modulation frequencies. An average value of absorption coefficient $\mu'_s$ at the wavelength of light used is then calculated. Measurements may be repeated using light of a different wavelengths.

Equations (10a)–(10d) also show that at fixed modulation frequency, $\omega$, the values of $$\ln\left(\frac{r}{r_0}DC_{rel}\right), \ln\left(\frac{r}{r_0}AC_{rel}\right),$$

$\ln(Mod_{rel})$ and $(PS_{rel})$ are linear functions of the difference of distance between detectors, $(r-r_0)$. From a plot of these values, $$\ln\left(\frac{r}{r_0}DC_{rel}\right), \ln\left(\frac{r}{r_0}AC_{rel}\right),$$

$\ln(Mod_{rel})$ and $(PS_{rel})$, as a function of $(r-r_0)$, the slopes can be determined from linear regression. We term these slopes, $K_{DC}$, $K_{AC}$, $K_{Mod}$ and $K_{PS}$, respectively. These slope are predictive of the optical properties, using the following equations:

$$K_{DC} = -\sqrt{3\mu_a(\mu_a+\mu_s')} \qquad (10a)$$

$$K_{AC} = -\sqrt{\frac{3}{2}\mu_a(\mu_a+\mu_s')}\left[\sqrt{1+\left(\frac{\omega}{v\mu_a}\right)^2}+1\right]^{1/2} \qquad (10b)$$

$$K_{Mod} = -\sqrt{\frac{3}{2}\mu_a(\mu_a+\mu_s')}\left[\sqrt{2}-\left(\sqrt{1+\left(\frac{\omega}{v\mu_a}\right)^2}+1\right)^{1/2}\right] \qquad (10c)$$

$$K_{PS} = \sqrt{\frac{3}{2}\mu_a(\mu_a+\mu_s')}\left[\sqrt{1+\left(\frac{\omega}{v\mu_a}\right)^2}-1\right]^{1/2} \qquad (10d)$$

If the refraction index of the medium is known, the absorption coefficient, $\mu_a$, and isotropic scattering coefficient, $\mu_s'$, can be determined given the modulation frequency, $\omega$. The advantage of the MD method is that an analytical solution of optical parameters can be directly derived from the above equations and nonlinear regression can be avoided.

The above four equations contain only two unknowns, and therefore, they are not independent. The following equation can be obtained from Equation (10) for checking the consistency of FDPM measurements:

$$\frac{K_{AC}^2 - K_{PS}^2}{K_{DC}^2} = K = 1 \qquad (11)$$

We term the criteria parameter for the MD method, K.

In practice, the values of $\mu_a$ and $\mu_s'$ can be obtained using four different linear regression strategies: simultaneous regression of (1) DC+AC; (2) DC+PS; (3) AC+PS; and (4) Mod+PS experimental data. From appropriate algebra transformation, the analytical solutions of optical parameters can be expressed as:

• AC-DC: (12a)

$$\mu_a = \frac{\omega n}{c}\left\{[2(K_{AC}/K_{DC})^2 - 1]^2 - 1\right\}^{-1/2} \quad \mu_s' = \frac{K_{DC}^2}{3\mu_a} - \mu_a$$

• DC-PS: (12b)

$$\mu_a = \frac{\omega n}{c}\left\{[2(K_{PS}/K_{DC})^2 + 1]^2 - 1\right\}^{-1/2} \quad \mu_s' = \frac{K_{DC}^2}{3\mu_a} - \mu_a$$

• AC-PS: (12c)

$$\mu_a = \frac{\omega n}{c}\left[\left(\frac{K_{AC}^2 + K_{PS}^2}{K_{AC}^2 - K_{PS}^2}\right)^2 - 1\right]^{-1/2} \quad \mu_s' = \frac{K_{AC}^2 - K_{PS}^2}{3\mu_a} - \mu_a$$

Where n is the refraction index of the scattering medium and c is the light speed in a vacuum.

For Mod and PS data, the analytical solution for the optical properties cannot be directly obtained owing to the lack of linear dependence on $\mu_a$:

$$\frac{K_{Mod}}{K_{PS}} = \frac{\sqrt{2}-\sqrt{T+1}}{\sqrt{T-1}} \text{ where } T = \sqrt{1+\left(\frac{\omega n}{c\mu_a}\right)^2} \qquad (12d)$$

However, the numerical solution of $\mu_a$ can be easily obtained, and $\mu_s'$ can be subsequently obtained from equation (10d). Values of $\mu_a$ and $\mu_s'$ can also be obtained from simultaneously regressing all AC, DC, and PS data by the least squares method.

Figure 5:
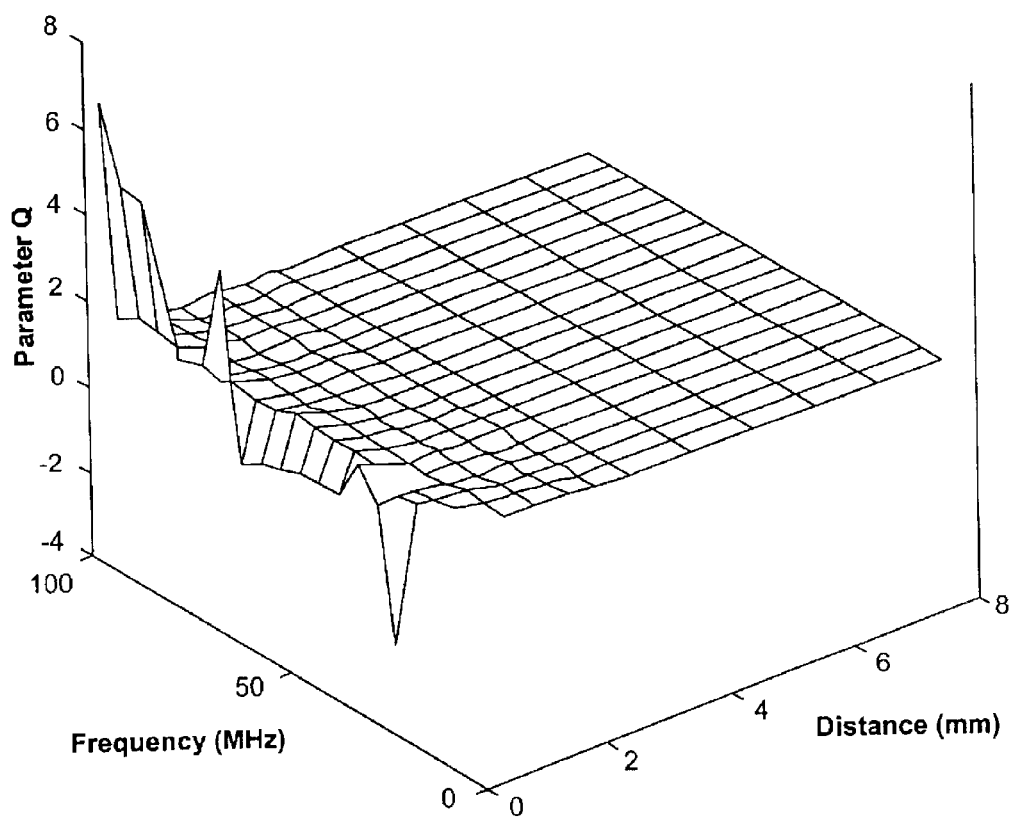
FIG. 5 shows an illustration of the values of the criteria parameter, Q, at different frequencies and distances from source to detector.

FIG. 5 illustrates use of the criteria parameter, Q, as a function of relative distance $r-r_0$ and modulation frequency $\omega$ for a typical FDPM measurement. Three experimental points at small relative distances $r-r_0$ and small frequencies $\omega$ are out of the range of this figure because the values of criteria parameter Q at these points are large. In this figure, the values of function Q are close to one for most of the experimental data with the exception of those data at small relative distances that are outside preferred operating conditions, and which satisfy the assumptions of the photon diffusion model. FIG. 5 illustrates typical experimental results. For each experiment, analysis of the criteria parameter provides information of: (1) whether abnormal measurement error exists during FDPM experiment; (2) which ranges of modulation frequency and relative distance are suitable for FDPM experiments with the particular sample; and (3) what parts of the measurement data can be used to give accurate and reliable optical properties. So Eq. 9 provides an important criterion to check the instrument performance, to avoid system and abnormal measurement error, and to find optimal operation conditions during FDPM measurements.

Compared with theoretical predictions, simultaneous regression of DC+PS, AC+PS or DC+AC+PS data can provide good derived optical parameters at high modulation frequency and large relative distances for both the MF and MD methods. In order to increase the signal-to-noise ratio, and to improve the accuracy and precision of parameter estimation, the MD and MF methods may be combined. For a MF measurement, the experiment can be performed at several different relative distances (called the combined MF method); while for a MD measurement, the experiment can be performed at several different modulation frequencies (called the combined MD method). The averaged accuracy and precision of estimated scattering coefficients using combined MF and MD measurements with different regression approaches and relative distances ranging from 2.5 mm to 8 mm for MF measurements and modulation frequencies ranging from 60 MHz to 100 MHz for MD measurements showed that these ranges avoid large noises arising at low frequencies and small relative distances ("Precise Analysis of Frequency Domain Photon Migration Measurements for Characterization of Concentrated Colloidal Suspensions," Rev. Sci. Instrum., 73(2): 383–393, 2002). Compared with MD and MF methods used alone, all these combined approaches can improve the accuracy and precision of estimated isotropic scattering coefficients. The averaged accuracy of the combined MD and MF methods are comparable to the uncertainty of the calculated $\mu_s'$ values by Mie theory (1.44%). Compared to the combined MF method, the combined MD method has advantages that it avoids the non-linear regression. Furthermore, linear plot and criteria parameter K (Eq. 11) can easily be used to check experiment conditions and consistency of experimental data with the MD method. Since simultaneous regression of DC+PS data or AC+PS data of combined MD measurements provides estimation of uncertainties of isotropic scattering coefficient by standard error analysis of a linear model, both regression strategies are preferred for data analysis.

When the final value of scattering coefficient of a sample is determined at a selected wavelength of the incident light, that value is inserted in equations that model the scattering properties of the colloidal sample to be investigated. The scattering properties depend on volume concentration of a disperse phase, the particle size distribution of the particles and, at higher volume concentrations, the interactions between the particles.

In past methods, the particle size distribution (PSD) of a sample has been assumed a priori to be either normal, log-normal or Weibull. The parameters that describe each of these distributions were determined by a best-fit procedure using non-linear least-squares regression. Using the following procedure, the particle size distribution of a sample can be determined without an a priori assumption.

For non-interacting suspension (i.e., for S=1), upon measuring isotropic scattering coefficients at different wavelengths using FDPM, the inverse problem of determining f(x) and φ requires solution of the integral equation (4). Eq. (4) can be generalized as the following set of integral equations, $$\mu_s'(\lambda_i) = \int_{a_1}^{a_2} K(x,\lambda_i) p(x) dx + e_i \quad i=1,2,\ldots M \tag{13}$$

where $K(x, \lambda_i)$ is the kernel function, which is given by:

$$K(x, \lambda_i) = \frac{3 Q_{scat}(\lambda_i, x)}{2x}[1 - g(\lambda_i, x)] \quad i = 1, \ldots, M \tag{14}$$

Here $\mu_s'(\lambda_i)$ is the discrete set of measurement data at M different wavelengths; p(x) is an unknown function to be determined; $a_1$ and $a_2$ are the size limits within which the size distribution lies; and $e_i$ is the measurement error.

Eqs (13) and (14) constitute the inversion problem for recovering an unknown function p(x) from discrete measurement data $\mu_s'(\lambda_i)$. In the method disclosed herein, the unknown function p(x) is the product, φf(x), instead of f(x) and φ individually, since f(x) and φ can be separated by the normalized distribution constraint:

$$\int \phi f(x) dx = \phi \tag{15}$$

The unknown function p(x) is approximated by a linear combination of B-spline base functions, $B_j^m(x)$, with coefficients, $c_j$, which are given by:

$$p(x) = \sum_{j=1}^{N} c_j B_j^m(x) + \varepsilon(x) \tag{16}$$

Here $\in(x)$ is the approximation error, and m, N are the order and dimension of the B-spline respectively. Since B-spline can accurately approximate any smooth finction, the use of B-spline functions reduces the number of independent variables to be determined and stabilizes the inversion process.

Using the B-spline approximation, Eq. 13 can be written as:

$$\mu_s'(\lambda_i) = \sum_{j=1}^{N} c_j \int K_i(x, \lambda_f) B_j^m(x) dx + E_i \quad i = 1, \ldots, M \tag{17}$$

where $E_i$ is the summation of measurement error and model (approximation) error. In matrix notation, equation (15) is given by:

$$b = Af + E \tag{18}$$

where b is the measurement data and $b_i = \mu_s'(\lambda_i)$; f is an unknown function and $f_j = c_j$; E is error; and A is the response model, whose components are:

$$a_{i,j} = \int K_i(x,\lambda_i) B_j^m(x) dx \tag{19}$$

In general, the solution to equation (18) can be formulated as a classical least squares problem:

$$\min\{\|Af-b\|_2^2\} \quad (20)$$

However, since direct solution of equation (19) can yield an unstable solution when measurement data is contaminated with noise, regularization is necessary for reducing the influence of the noise in the inversion process.

To stabilize the inverse solution, we employ Tikhonov regularization in which the regularized solution $f_\alpha$ is defined as the solution of the following optimizing problem:

$$\min\{\|Af-b\|_2^2 + \alpha^2\|Lf\|_2^2\} \quad (21)$$

Here L is an appropriately chosen regularization matrix. The regularization parameter $\alpha$ controls the weight given to minimization of the regularization term, $\|Lf_{reg}\|_2$, relative to minimization of the residual term, $\|Af_{reg}-b\|_2$.

Different ways to choose the regularization matrix L result in different regularization methods, such as zeroth, first, and second order, and entropy regularization. In the method disclosed herein, the second order regularization form is chosen since it provides the smoothness of the solution, which is often called a smoothing constraint:

$$\|Lf_{reg}\|_2^2 = \sum_{j=3}^{N} (f_j - 2f_{j-1} + f_{j-2})^2 \quad (22)$$

However, the smoothing constraint alone cannot guarantee stable, non-negative solutions of the size distribution. To avoid a negative solution, the non-negativity constraint should be included:

$$p(x) = \sum_{j=1}^{N} f_j B_j^m(x) \geq 0 \quad (23)$$

Equations (21), (22) and (23) constitute the inverse problem in which coefficient f of the B-spline expansion needs to be determined. From equations (15) and (16), the PSD and volume fraction are subsequently obtained. If the regularization parameter $\alpha$ is known, the inverse problem is a linear least squares problem with linear inequality. The active-set quadratic programming (QP) method may be used to solve the PSD inverse problem. The success of this regularization method depends on the choice of optimal regularization parameter $\alpha$.

The choice of optimal regularization parameter is important to solve the ill-posed inversion problem. On one hand, if the parameter is too small, the noise cannot be filtered out and spurious oscillations in the solution exist. On the other hand, if the parameter is too large, some data are filtered out as well as noise and the solution is over-smoothed.

If information about error norm $\|E\|_2$ (including model and experimental errors) is available, the discrepancy principle can be used to choose regularization parameters, such that the residual norm for the regularized solution equates the error norm. However, this technique clearly depends on the ability to correctly estimate errors in the measurement data. Generalized cross validation (GCV) is a popular method for choosing the regularization parameter since it does not require an estimation of the error norm. The GCV method is based on statistical considerations that a good regularization parameter can predict missing data values. However, GCV cannot be expected to perform well in the case where there are relatively few measurements and the GCV function may have a flat minimum. Consequently it may be difficult to locate the value of a global minimum.

Figure 6:
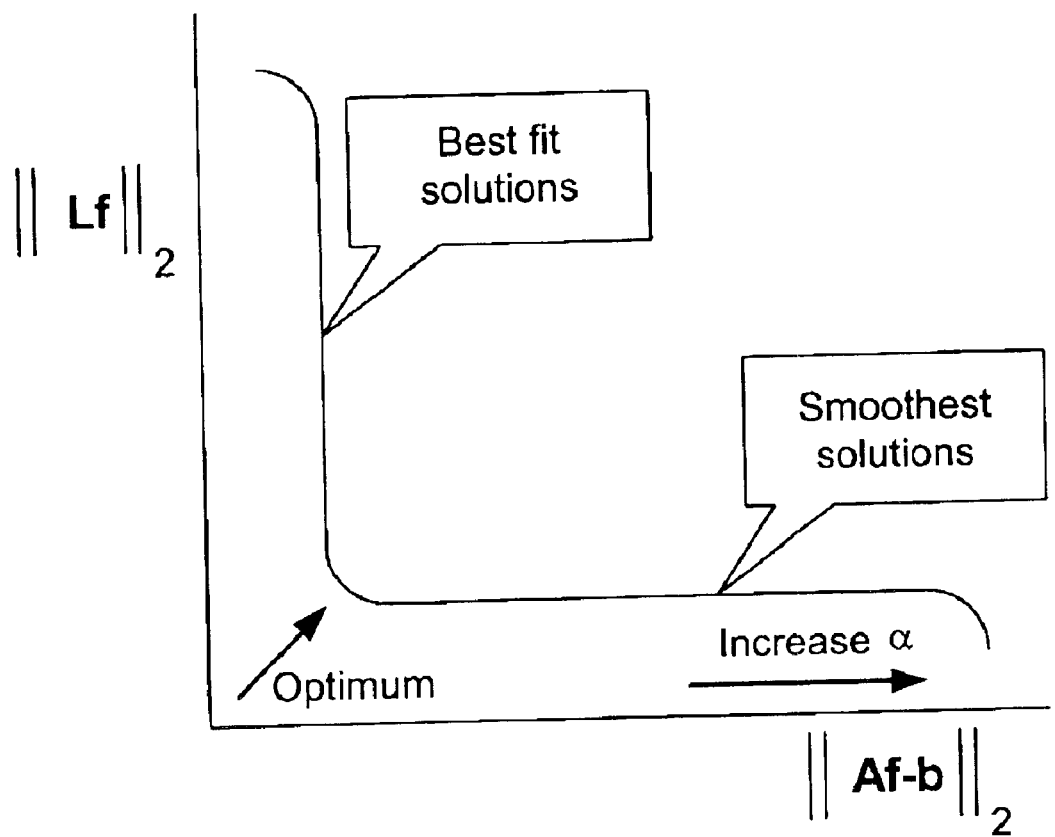
FIG. 6 shows an "L-curve" used for parameter-choosing method for regularization of the solution of the inversion problem for particle size distribution.

The L-curve method is another parameter-choosing method that is independent of error estimates. The L-curve is a plot of regularization term $\|Lf_{reg}\|_2$ versus residual term $\|Af_{reg}-b\|_2$ for all regularization parameters. As shown in FIG. 6, an optimal solution lies near the corner of the "L-curve" since the solution strikes a balance between the solution smoothness and the residual error in this region. In most applications, the L-curve method is used for regularization methods which employ a smoothing constraint only. In the method disclosed herein, the L-curve method is used to choose the regularization parameter for the PSD inversion problem contained by both smoothness and non-negativity constraints. Results of numerical simulation to investigate the performance of the method are reported in the paper "Inversion Algorithms for Particle Sizing with Photon Migration Measurement," *AIChE J.*, July, 2001, Vol. 47, No. 7, pp. 1487–1498, which is incorporated by reference herein.

Figure 7:
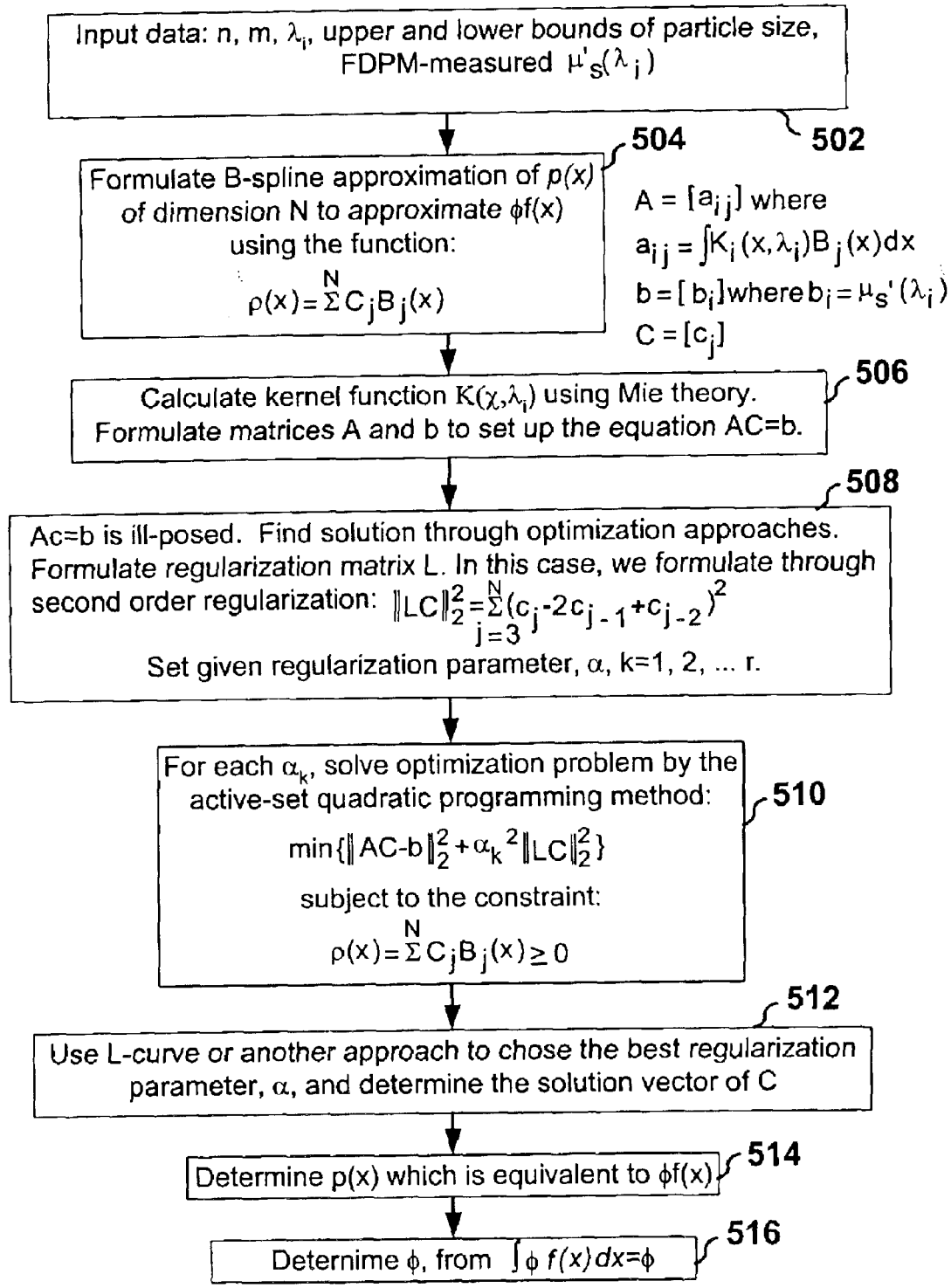
FIG. 7 illustrates a flowchart showing one embodiment of a method for determining particle size distribution and volume fraction of a suspension of non-interacting particles from scattering coefficients.

FIG. 7 shows a flowchart of the method for determining volume fraction and particle size distribution for a sample of non-interacting particles having any size distribution—single modal or multi-modal. If it is suspected that the particles in a sample may not have a simple particle size distribution, i.e., may be polydisperse or multi-modal, the procedure of FIG. 7 should be used in analysis of the scattering data. The method is described in the paper "Inversion Algorithms for Particle Sizing with Photon Migration Measurement," *AIChE J.* Vol. 47, No. 7, 1487 (July 2001).

Referring to FIG. 7, in step 502, values of refractive indices, wavelength of the incident light, the measured value of scattering coefficient and an estimate of the upper and lower bounds of particles sizes in the sample are entered. In step 504, an approximation of the unknown function p(x) is expressed as a linear combination of B-spline base functions with coefficients c. The value of N is to be no greater than the number of wavelength measurements. In step 506, kernel function K is calculated using Mie theory, which is well known in the art. Matrices A and b are then formulated as shown in the figure. In step 508 an optimization procedure employing a regularization matrix L is used with second order regularization. Then in step 510, the optinization problem is solved by an active-set quadratic programming method, as shown. In step 512, an L-curve or another approach is used to choose the best regularization parameter and to determine the solution vector C. In step 514 the value of p(x) is determined, and in step 516 the value of volume fraction is determined by integrating the function p(x).

Simulation studies showed that: (1) the B-spline expansions provide a good approximation of size distributions; (2) the inversion algorithm can accurately recover the PSD and volume fraction if there is no measurement error; and (3) the effects of model errors can be neglected, reducing the need for regularization significantly. The use of the B-spline on actual experimental data is also demonstrated in the paper "Inversion Algorithms for Particle Sizing with Photon Migration Measurement," *AIChE J.*, July, 2001, Vol. 47, No. 7, pp. 1487–1498.

The inverse algorithm can effectively suppress noise propagation, and provide reasonable inversion results for normal and log-normal distributions within as high as 10% measurement error in isotropic scattering coefficients. As the noise level increases, the size distributions are over-smoothed, which may be due to the L-curve method. Although the accuracy of recovered size distributions decreases as the noise level increases, the recovered volume fractions are accurate, and the moments of recovered PSD (i.e., mean size and standard deviation) are close to the true values.

From solutions using synthetic measurements, both the smooth and non-negativity constraints are important for PSD inversion from FDPM measurements. The original Tikhonov regularization method does not include the non-negativity constraints. When used in the inverse solution for FDPM measurements, it produces unrealistic negative solutions, especially at the limits of particle size distribution.

As described in the paper "Inversion Algorithms for Particle Sizing with Photon Migration Measurement," *AIChE J*., July, 2001, Vol. 47, No. 7, pp. 1487–1498, two Gaussian size-distributions with the same mean sizes but different standard deviations, using synthetic measurements, showed that at noise levels of 1%, 5% and 10%, the effects of polydispersity on the quality of inversion are small, and the method described herein can recover both narrow and broad distributions at different noise levels. Also, the method disclosed herein can recover a bimodal size-distribution. The recovered results were in good agreement with assumed true values for the bimodal size distribution and the model errors were negligible. Furthermore the results demonstrate that the a priori assumption of a PSD can be avoided.

A study of the effects of measurement errors for bimodal size distribution showed that at low noise level (less than 5%), the first mode shows good agreement with the true value, while the second mode is far away from the true value. Compared to the inversion of unimodal normal distribution, the effects of noise are larger for recovery of bimodal normal distributions, which means that recovery of multi-modal distribution is more sensitive to measurement error than recovery of a unimodal distribution. Hence, more accurate and more numerous measurement data are required in order to recover a multi-modal size distribution. Although agreement between retrieved PSD and assumed PSD decreases as noise level increases, the two modes of distribution can be successfully reconstructed with random measurement error as high as 10%.

Examples of recovery of PSDs for both synthetic data and experimzental data are provided in the paper "Inversion Algorithms for Particle Sizing with Photon Migration Measurement," *AIChE J*., July, 2001, Vol. 47, No. 7, pp. 1487–1498. Particle-sizing results for experimental data on titanium dioxide samples are compared with results of previous methods using dynamic light scattering and X-ray measurements.

The procedure described in FIG. 7 is applicable to samples at volume concentrations low enough such that particles are non-interacting. When particles are interacting, the nature of interaction forces between the particles can also be investigated by FDPM measurements using Eq. 5, but the partial structure factor, $S_{i,j}$, included in the equation, which is a direct measure of the local ordering of colloidal particles, will become less than unity.

For a polydisperse system, since particle interactions occur between colloids not only with the same particle size but also with different particle sizes, the partial structure factor, $S_{i,j}$, should be considered, where i and j represent particles with different sizes.

Although the form factor, $F_{i,j}$, in Eq. 5 can be calculated by classical Mie scattering theory, it is difficult to extract the partial structure factor, $S_{i,j}$, from Eq. (5) using the measured isotropic scattering coefficient, $\mu_s'$, from FDPM measurements at several different wavelengths, owing to ill-posedness of the Fredholm integral equation. Instead, the angle-integrated structure factor, $\langle S(q) \rangle$, can be defined from the ratio of scattering coefficients computed or. measured when particle interactions are accounted for (i.e., $\mu'_{s,interacting}$) and when they are not (i.e., $\mu'_{s,non-interacting}$):

$$\langle S(q) \rangle = \frac{(\mu_s')_{interacting}}{(\mu_s')_{non-interacting}} = \qquad(24)$$

$$\frac{\int_0^\pi \sin\theta(1-\cos\theta)\int_0^\infty \frac{f(x_i)}{x_i^3}\int_0^\infty \frac{f(x_j)}{x_j^3}F_{i,j}(n,x_i,x_j,\lambda,\theta) - S_{i,j}(n,x_i,x_j,\lambda,\theta)dx_j dx_i d\theta}{\int_0^\infty \frac{f(x)}{x^3}\int_0^\pi F(n,x,\lambda,\theta)\sin\theta(1-\cos\theta)d\theta dx}$$

Hence, the angle-integrated structure factor $\langle S(q) \rangle$ can be experimentally obtained using FDPM-measured $\mu'_s$ of concentrated suspensions as well as from theoretical prediction from a model of particle interaction or partial structure factor, $S_{ij}$. By comparing angle-integrated structure factors obtained experimentally with that those theoretically predicted, one can examine the model of $S_{ij}$ to investigate particle-particle interactions in colloidal suspensions. We found that particle interactions arise primarily due top the excluded volume interaction at high volume fractions, and the polydisperse hard sphere Percus-Yevick (HSPY) model is suitable for accounting for particle interactions in dense, polydisperse suspensions.

For an interacting system, if the form of PSD is known (e.g., Gaussian, log normal, etc.), we can recover the PSD and volume fraction by regressing the unknown parameters of PSD using nonlinear optimization methods. The algorithm to solve this inverse problem involves the minimization of a merit function, $\lambda^2$:

$$\chi^2 = \sum_{j=1}^M \left[(\mu_s')_j^O - (\mu_s')_j^C\right]^2 \qquad(25)$$

where $(\mu_s')_j^o$ is the experimentally observed scattering coefficient and $(\mu_s')_j^c$ is the value calculated from equation (5), based on the current guess for size distribution f(x).

Figure 8:
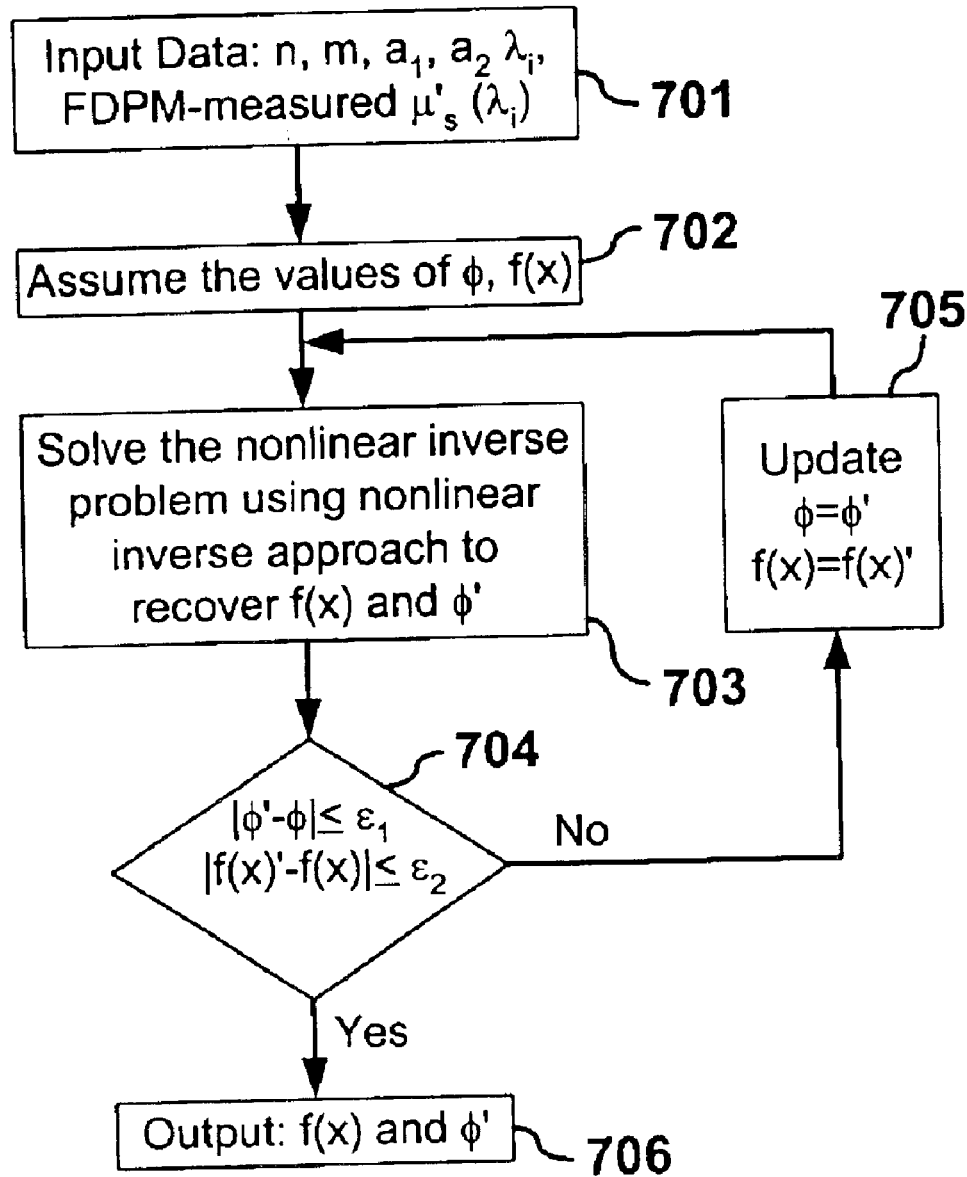
FIG. 8 illustrates a flowchart showing one embodiment of a method for solving the non-linear inverse problem for any arbitrary model of interaction between particles, whether purely volume exclusion or including attractive and repulsive forces.

If the form of PSD is unknown, for interacting systems, Eq. (5) is to be solved for recovery of volume fraction $\phi$ and particle size distribution, f(x). Since $S_{i,j}$ is a function of unknown $\phi$, Equation (5) is a nonlinear Fredholm integral equation. A general method for solving the non-linear inverse problem for any arbitrary model is illustrated in FIG. 8. In step 701, data and the measured value of the scattering coefficient at a selected wavelength are input. In step 702, values of $\phi$ and f(x) are assumed. In step 703, the nonlinear inverse problem is calculated to recover values of f(x) and $\phi'$. In step 704, recovered values are compared with assumed values. If the difference is not less than a selected value, update values are then selected in step 705. If the difference is less than the selected value, values of f(x) and $\phi$ are output in step 706.

In order to avoid solving a nonlinear inverse problem directly, several approximations, such as the Decoupling Approximation (DA) and the Local Monodisperse Approximation (LMA), can be used to simplify the complicated polydisperse Hard Sphere Percus-Yevick (HSPY) model to account for volume exclusion. In the DA model, it is assumed that the positions of the particles are independent of their size so that the partial structure factor is given by:

$$S_{i,j}(n,\lambda,x_i,x_j,\phi) = S(n,\lambda,\bar{x},\phi) \qquad(26)$$

where $\bar{x}$ is the average diameter of all colloids in the polydisperse system. For the LMA model, it is assumed that the positions of particles are completely correlated with their sizes so that each particle is surrounded by particles with the same size. The partial structure factor in the LMA model can therefore be written as:

$$S_{i,j}(n, \lambda, x_i, x_j, \phi) = \begin{cases} S_i(n, \lambda, x_i, \phi) & i = j \\ 0 & i \neq j \end{cases} \quad (27)$$

In both DA and LMA models, the effective structure factor can be calculated by the monodisperse HSPY model. Correspondingly, Equation (5) can be written as:

$$\mu'_s(\lambda) = \int_0^\infty \frac{12\phi f(x)}{k^2 x^3} \left[ \int_0^\pi F(n, x, \lambda, \theta) S(n, x_{\mathit{eff}}, \lambda, \phi_{\mathit{eff}}) \sin\theta (1 - \cos\theta) d\theta \right] dx \quad (28)$$

where $x_{\mathit{eff}}$ and $\phi_{\mathit{eff}}$ are the effective diameter and volume fractions that arise due to particle interactions, and $\phi = \phi_{\mathit{eff}}/(x_{\mathit{eff}}/x)^3$. For the DA model, we assume that $x_{\mathit{eff}} = \bar{x}$, since the approximation simply states that all interactions are approximated by the interactions of particles of the mean size of the distribution. For the LMA model, we assume: $x_{\mathit{eff}} = x$, and that only like particles of the same size interact. Hence the volume fraction $\phi_{\mathit{eff}}$ is essentially the volume fraction of particles with $x_{\mathit{eff}}$.

Figure 11:
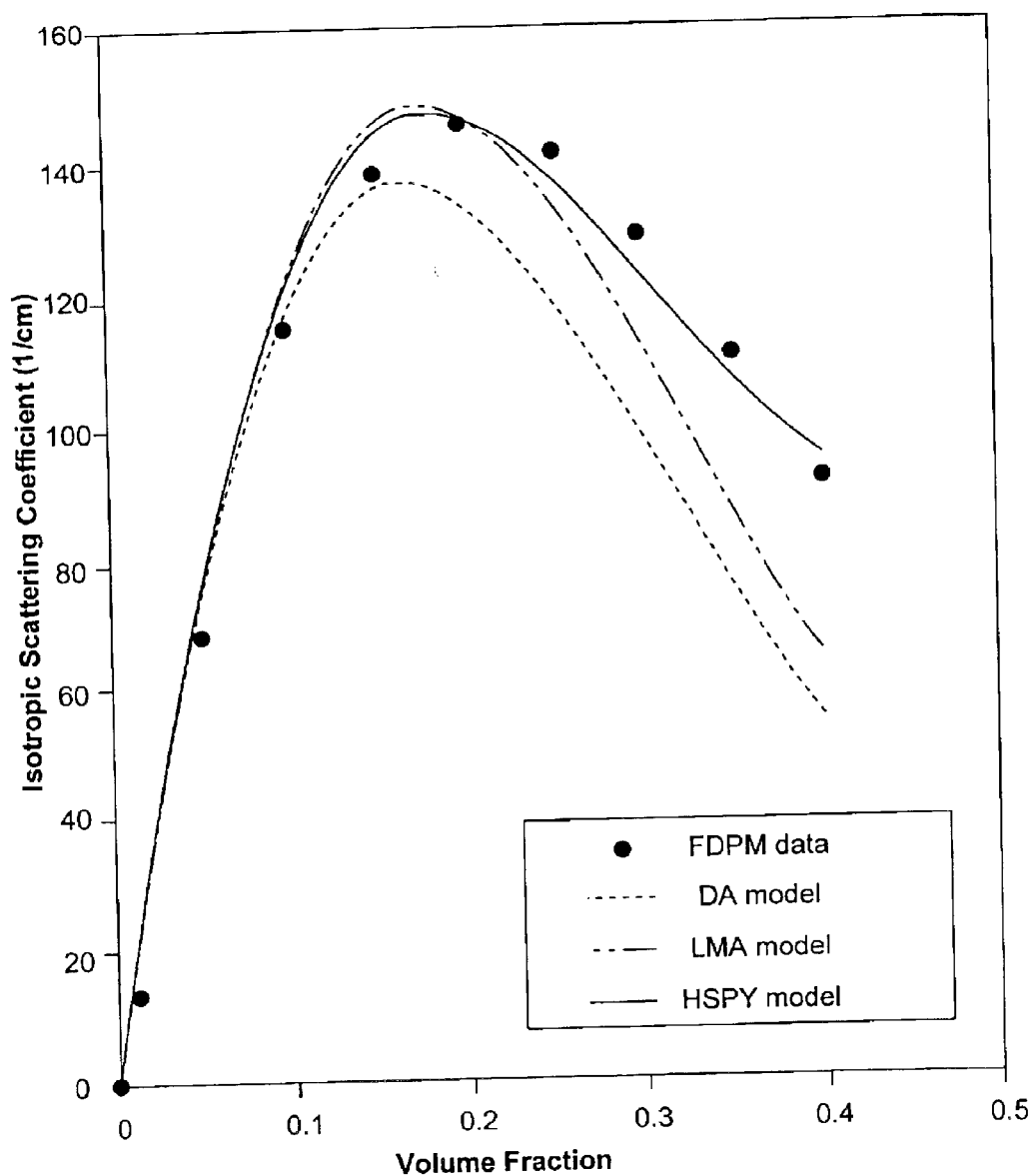
FIG. 11 shows a comparison of different structure factor models with FDPM data at a wavelength of 687 nm.

The DA and LMA models have been examined by FDPM measurements in dense surfactant-stabilized suspensions of polystyrene, and examples of model comparisons are shown in FIG. 11, from the paper "Approach for Particle Sizing in Dense Polydisperse Colloidal Suspension Using Multiple Scattered Light," Langmuir 2001, 17, 6142–6147, which is incorporated by reference herein. The figure shows that, at volume fractions <0.1 the DA model is a good approximation to the data and the HSPY model. Similar results can be inferred for the LMA model if the volume fraction is less than 0.2. The mismatch between predictions by the DA and the LMA models and experimental data at high volume fractions is due to the fact that the effective diameter of the particles, because of particle interactions, cannot be assumed to equal their physical diameter. Correspondingly, if we introduce the interaction parameter, which is defined as $\beta = x_{\mathit{eff}}/\bar{x}$ for the DA model, or $\beta = x_{\mathit{eff}}/x$ for the LMA model, the accuracy of the DA and the LMA models can be significantly improved. Table 1 illustrates the interaction parameters, $\beta$, of the DA and LMA models by fitting FDPM experimental data to the models with known volume fraction and PSD, where experimental data measured at wavelengths of 687 nm and 828 nm were obtained from the same samples. We can see that, at each volume fraction, the interaction parameters fitted from independent data acquired at two different wavelengths are in close agreement. This indicates that, by introducing the interaction parameter, the DA and LMA model can accurately predict the FDPM experimental data even at high volume fractions (>0.25).

Figure 9A:
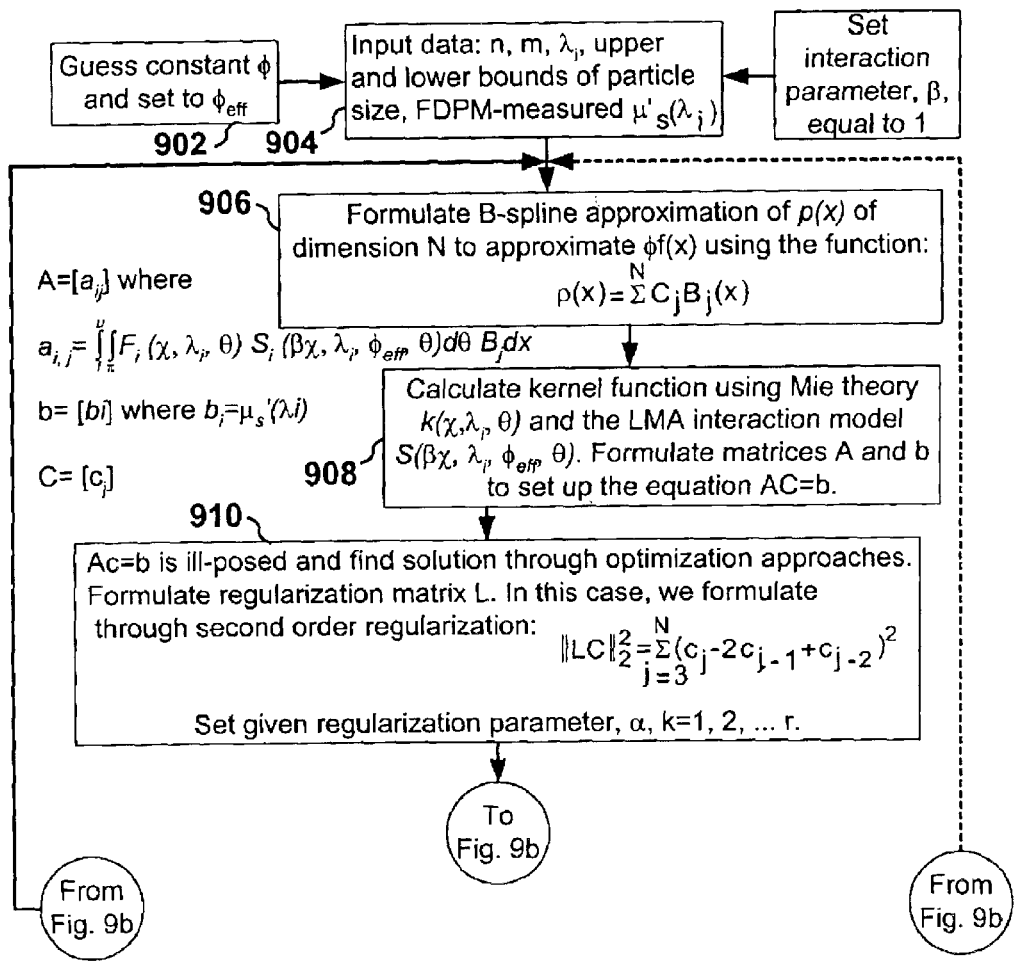
FIG. 9(a) and FIG. 9(b) show a flowchart of the linear approach associated with the LMA approximation for determining particle size distribution, volume fraction and interaction parameter for a suspension of particles which interact through volume exclusion.
Figure 9B:
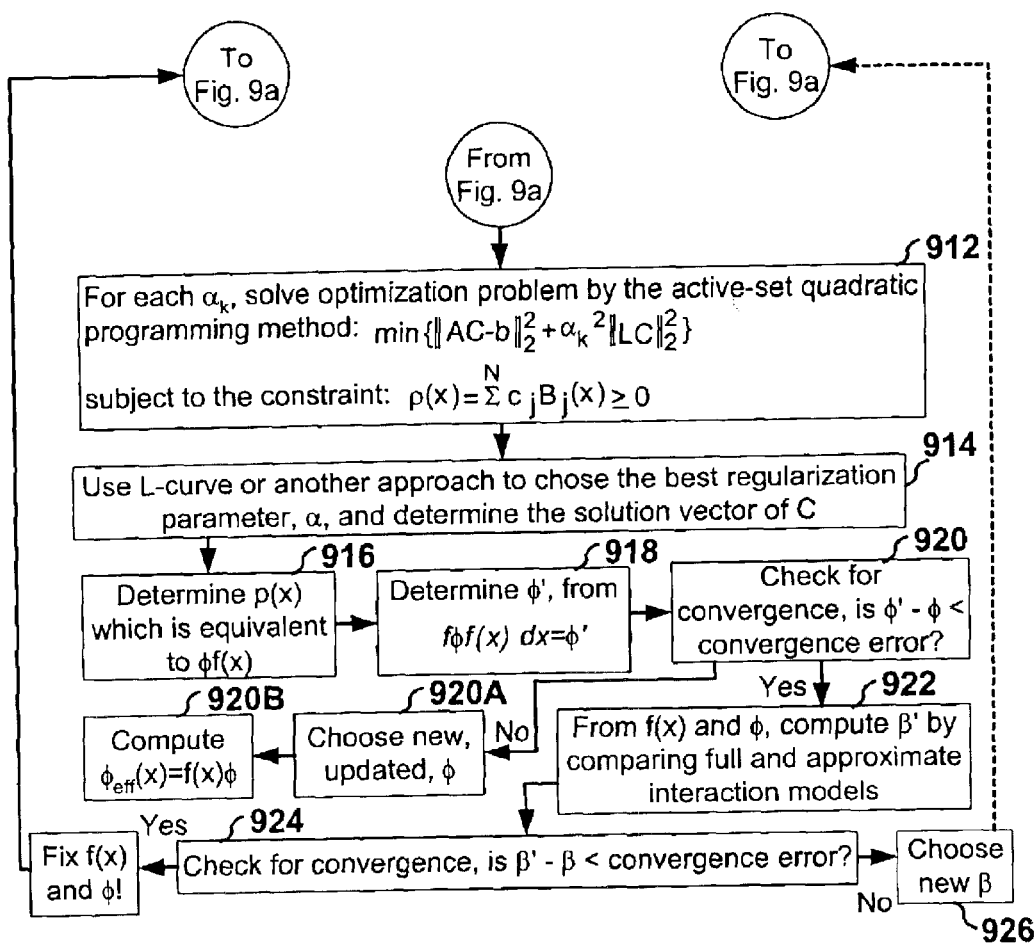

A flowchart for determining $\phi$, $f(x)$ and $\beta$ using the LMA model is shown in FIG. 9(a) and FIG. 9(b). The parameter $\beta$ is set equal to 1 and in step 902 an initial value of $\phi$ is guessed and set equal to $\phi_{\mathit{eff}}$. In step 904, input physical data, measured data and assumption are input as shown. In step 906, a B-spline approximation of p(x) of dimension N is introduced. In step 908, the kernel function from Mie theory is calculated and S is calculated from the LMA model, using matrices as shown in the figure. In step 910, the optimization approach is used with use of matrix L and second order regularization. In step 912 the optimization problem is solved using the equations shown and the non-negative constraint of p(x). In step 914 the L-curve or an alternate approach is used to choose the best regularization parameter.

In step 916, p(x) is calculated. In step 918, the value of resulting $\phi$ is calculated, called $\phi'$. In step 920, the calculated value of $\phi$ is compared with the initial assumed value to determine if the difference is less than the convergence error. If it is not, in step 920A a new value of $\phi$ is chosen and a new value of $\phi_{\mathit{eff}}$ is calculated in step 920B. If the difference is less than convergence error, the value of $\beta'$ is calculated in step 922. The check for convergence of $\beta$ is determined in step 924. If the difference is greater than convergence error, a new value of $\beta$ is chosen in step 926. If it is not, then the final values of $f(x)$, $\phi$ and $\beta$ have been determined.

Figure 10A:
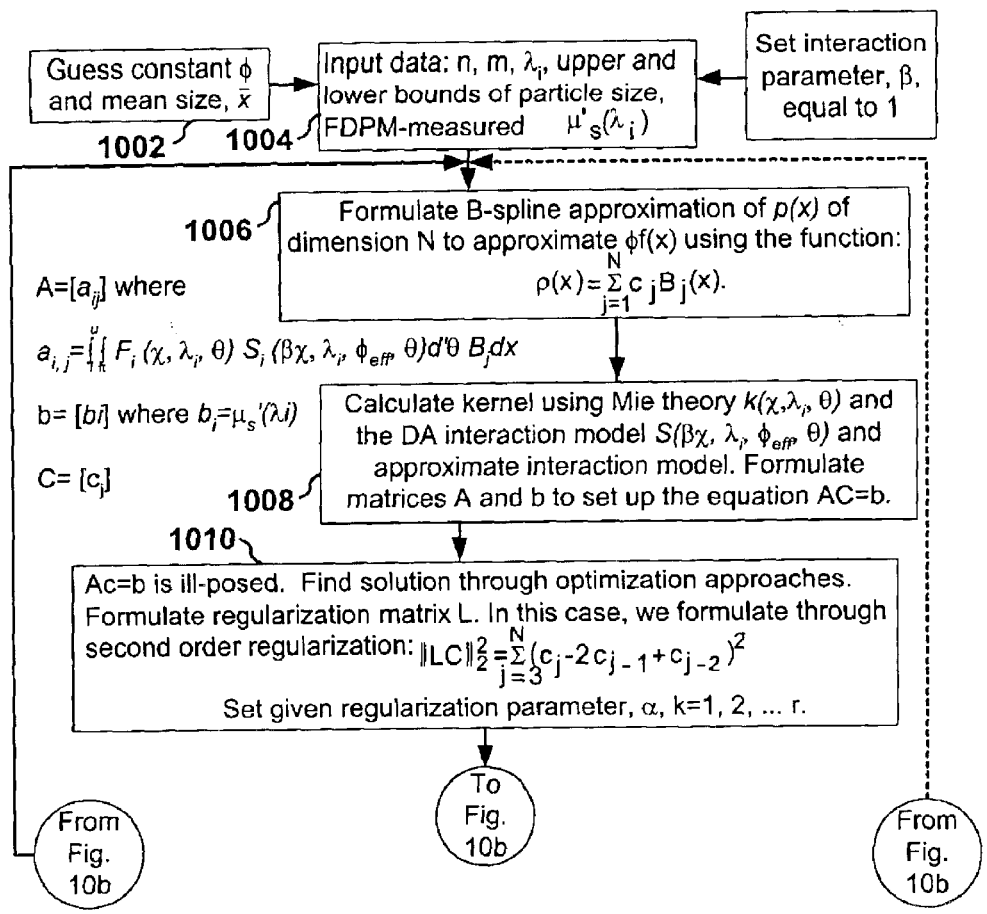
FIG. 10(a) and FIG. 10(b) show a flowchart of the linear approach associated with the DA approximation for determining particle size distribution, volume fraction and interaction parameter for a suspension of particles which interact through volume exclusion.
Figure 10B:
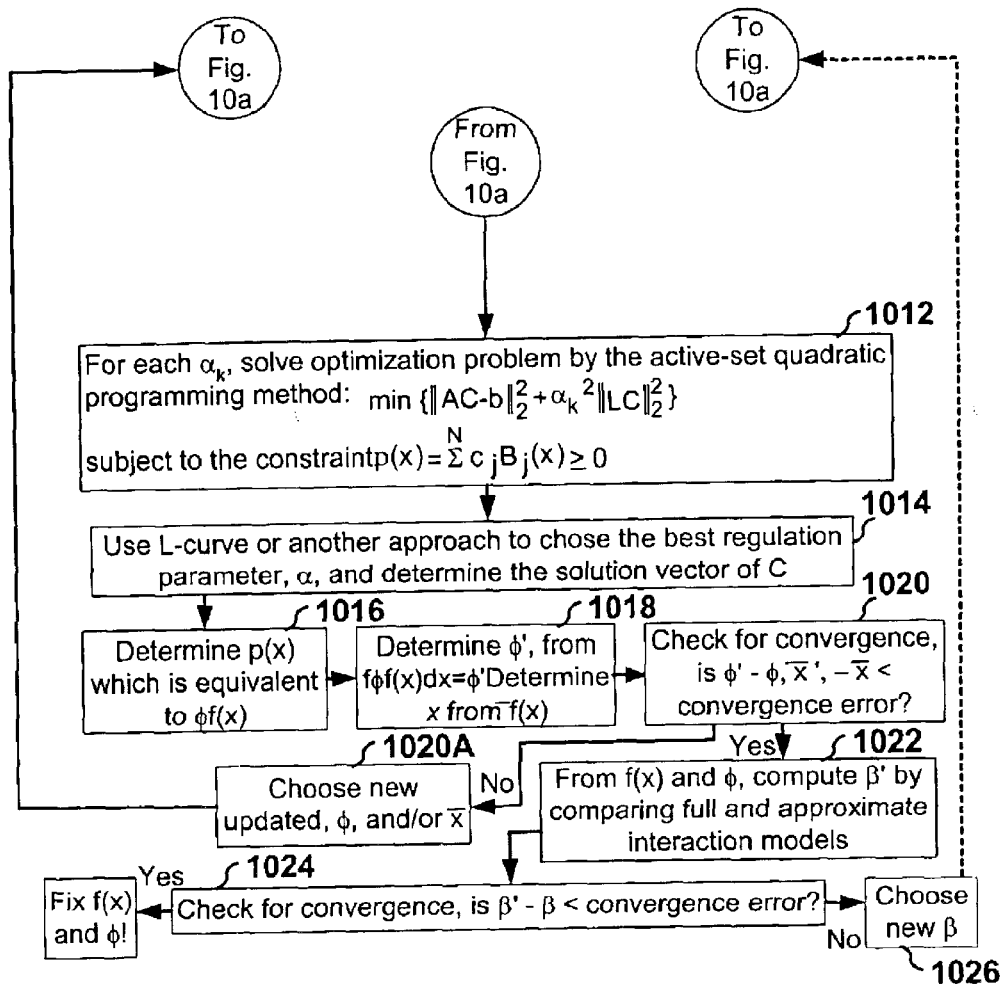

Similarly, a flowchart for determining $\phi$, $f(x)$ and $\beta$ using the DA model is shown in FIG. 10. The parameter $\beta$ is set equal to 1 and in step 1002 an initial value of $\phi$ and a mean size (x bar) are guessed. In step 1004, input physical data, measured data and assumptions are input as shown. In step 1006, a B-spline approximation of p(x) of dimension N is introduced. In step 1008, the kernel function F from Mie theory is calculated and S is calculated from the DA model, using matrices as shown in the figure. In step 1010, the optimization approach is used with use of matrix L and second order regularization. In step 1012 the optimization problem is solved using the equations shown and the non-negative constraint of p(x). In step 1014 the L-curve or an alternate approach is used to chose the best regularization parameter and the solution vector. In step 1016, p(x) is calculated. In step 1018, the value of resulting $\phi$ is calculated, called $\phi'$. Also, (x bar) is calculated from f(x). In step 1020, the calculated value of $\phi$ is compared with the initial assumed value to determine is the difference is less than the convergence error. If it is not, in step 1020A a new value of $\phi$ and/or (x bar) is chosen and input at step 1006. If the difference is less than convergence error, the value of $\beta'$ is calculated in step 1022. The check for convergence of $\beta$ is determined in step 1024. If the difference is greater than convergence error, a new value of $\beta$ is chosen in step 1026. If it is not, then the final values of $f(x)$, $\phi$ and $\beta$ have been determined.

TABLE 1

| Volume fraction | Interaction parameter (DA model) | | Interaction parameter (LMA model) | |
|---|---|---|---|---|
| | 687 nm | 828 nm | 687 nm | 828 nm |
| 0.0510 | 1.127 | 1.069 | 1.161 | 1.096 |
| 0.1007 | 1.017 | 1.014 | 1.048 | 1.038 |
| 0.1516 | 0.994 | 0.992 | 1.021 | 1.013 |
| 0.2017 | 0.976 | 0.978 | 1.002 | 0.996 |
| 0.2536 | 0.964 | 0.963 | 0.988 | 0.979 |
| 0.3015 | 0.958 | 0.958 | 0.979 | 0.972 |
| 0.3531 | 0.953 | 0.954 | 0.971 | 0.966 |
| 0.4032 | 0.949 | 0.949 | 0.965 | 0.959 |

EXAMPLE

A polydisperse sample of concentrated, surfactant stabilized, polystyrene suspension was provided by Dow Chemical, Midland, Mich., and used as received. The mean particle size, deviation and polydispersity of the polystyrene sample were measured by using DLS (ZETASIZER 3000, Malvern Instruments, U.K.) at dilute suspensions (~0.01%), and the results are shown in Table 2.

TABLE 2

|  | Mean (nm) | size Deviation (nm) | Polydispersity (%) |
| --- | --- | --- | --- |
| DLS results | 143.5 ± 0.5 | 24.0 ± 1.2 | 16.7 ± 0.8 |

FDPM measurements were conducted at various particle concentrations ranging from 5% to 40% solids by volume. The stock solutions were diluted by deionized ultra filtered (DUF) water. The exact volumne fractions of samples were determined by evaporation measurements, and are shown in Table 3.

TABLE 3

| Crude volume fraction | 5% | 10% | 15% | 20% | 25% | 30% |
| --- | --- | --- | --- | --- | --- | --- |
| Exact volume fraction | 5.10% | 10.07% | 15.16% | 20.17% | 25.36% | 30.15% |

Based on the photon diffusion model, several different experimental approaches and regression strategies were used to determine the absorption coefficient $\mu_a$, and isotropic scattering coefficient, $\mu'_s$. In the experiments, multiple distance (MD) measurements were performed at twelve different source-detector distances, ranging from 7 mm to 11 mm. In order to improve the precision and accuracy, MD measurements were performed at several different modulation frequencies ranging from 50 to 100 MHz. The average of FDPM-determined optical parameters and their uncertainties were calculated in order to decrease measurement errors. This method may be called the combined MD measurement, and gives the highest accuracy and precision of isotropic scattering coefficients.

Figure 12:
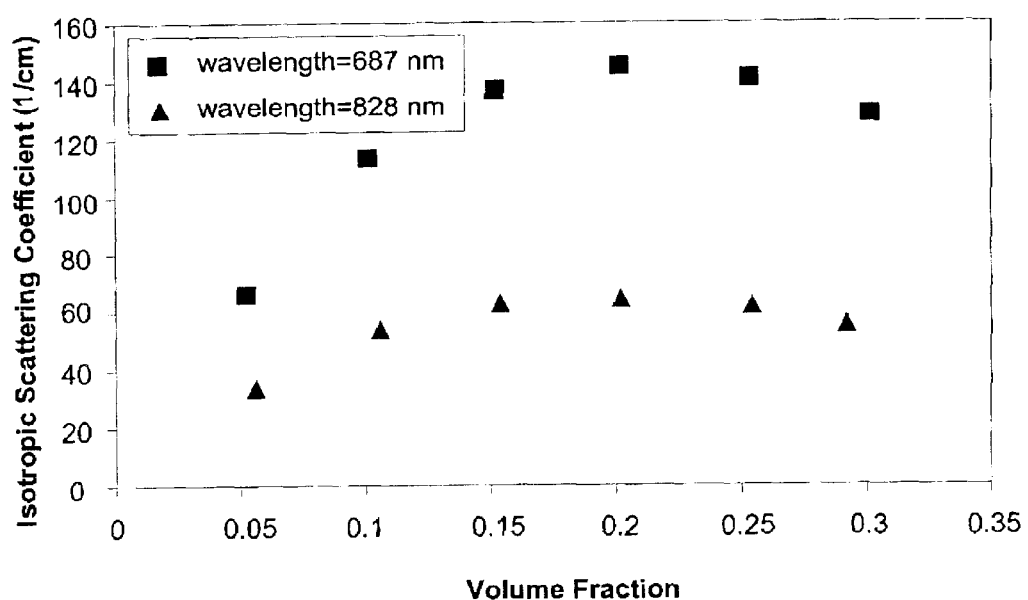
FIG. 12 shows the change of FDPM-measured scattering coefficients with volume fractions at two wavelengths.

FIG. 12 illustrates a plot of isotropic scattering coefficient measured by FDPM measurements as a function of volume fraction 0 for the latex samples at two different wavelengths.

Figure 13:
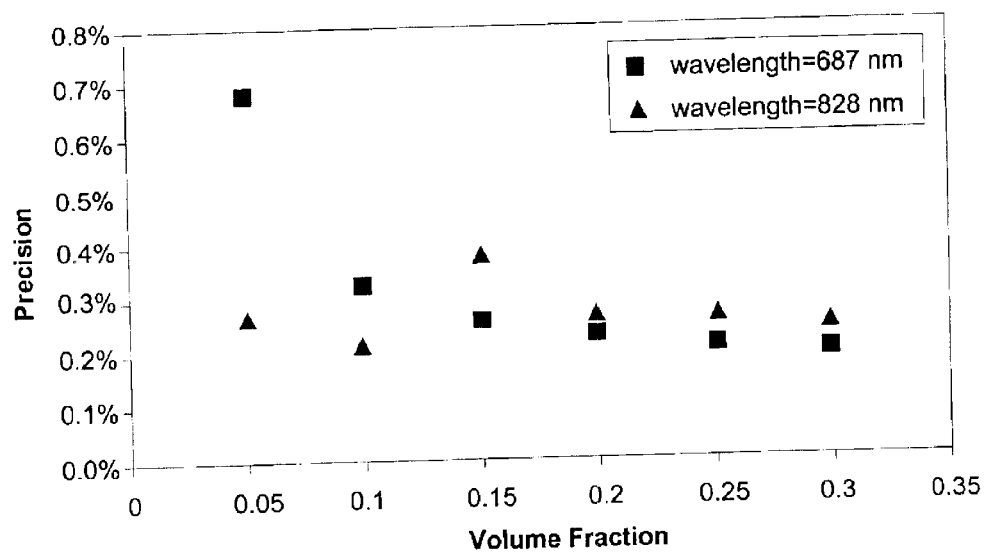
FIG. 13 shows the changes of precision of FDPM-measured scattering coefficients with volwne fraction at two wavelengths.

Besides the isotropic scattering coefficients, their uncertainties can also be derived from FDPM experimental dat FIG. 13 illustrates the precision of the FDPM-measured scattering coefficients at two wavelengths and a series of volume fractions. Here, the precision is defined as relative standard deviation of regressed isotropic scattering coefficients. The results show that the precision of FDPM-measured isotropic scattering coefficients is less than 0.4% at both wavelengths in all the measurements except at the lowest volume fraction.

Figure 14:
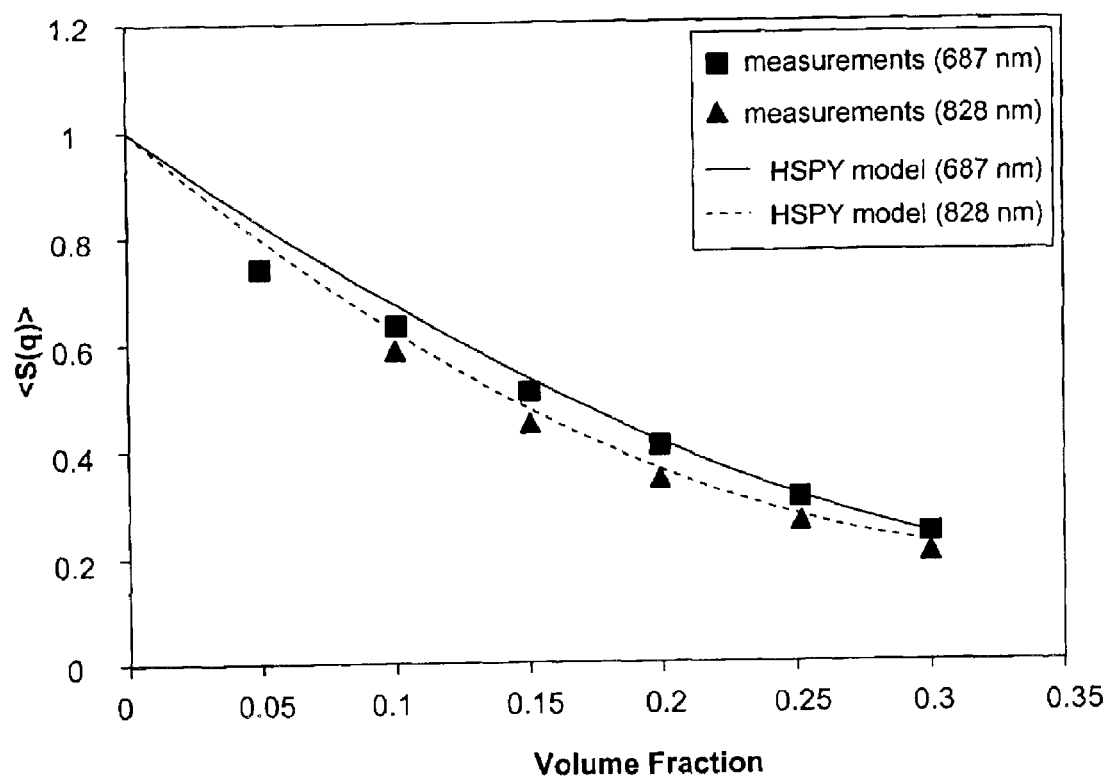
FIG. 14 shows the change of angle-integrated structure factors with volume fractions at two wavelengths for latex samples.

Using FDPM-measured isotropic scattering coefficients, the angle-integrated structure factor, $<S(q)>$, was experimentally determined using Eq. 24. FIG. 14 illustrates a plot of $<S(q)>$ as a function of volume fraction at two wavelengths for latex samples. The theoretical predictions using the polydisperse HSPY model, also shown in FIG. 14, indicate that the HSPY model represents a good approximation for description of particle interactions. Although small differences are observed between the experimental results and theoretical predictions, our results show that: (1) angle-integrated structure factors decrease with increasing volume fractions at the same wavelength due to the fact that particle interactions become more significant with increasing volume fraction; and (2) angle-integrated structure factors decrease with increasing wavelength at the same volume fraction due to the fact that as wavelength decreases, wave vector increases and $<S(q)>$ become larger. The small differences between the experimental results and theoretical predictions may be due to: (1) the existence of other types of particle interactions; and (2) possible discrepancies of DLS-measured mean size of latex particles used for calculation of $\mu'_s$, which would not be accounted for in this analysis. Nonetheless, FIG. 14 shows that particle interactions arise primarily due to the excluded volume interaction at high volume fractions, and the polydisperse HSPY model is suitable for accounting for particle interactions in this polydisperse latex sample.

Figure 15:
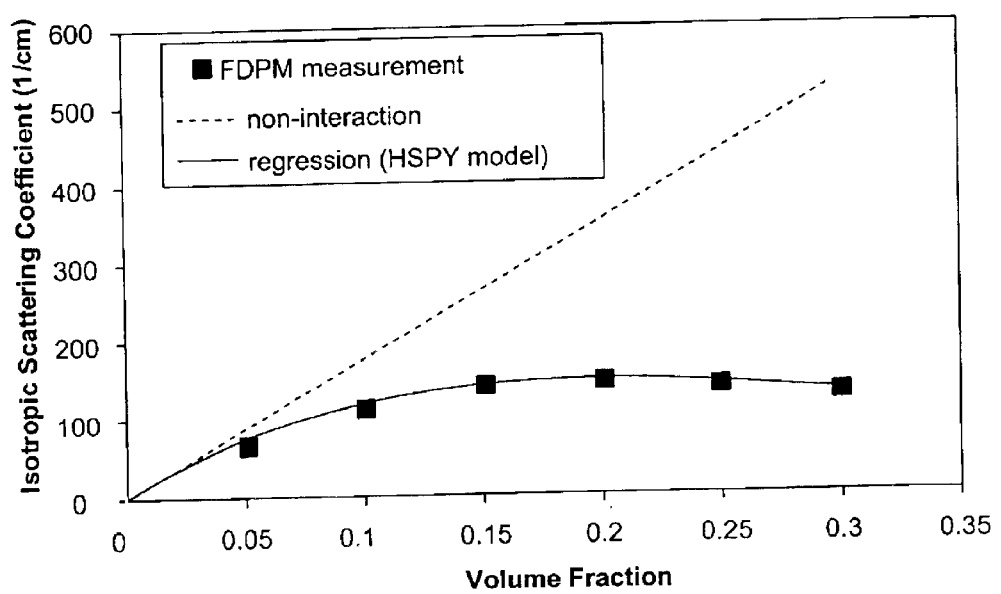
FIG. 15 shows the change of scattering coefficient with volume fraction for a polydisperse latex sample at a wavelength of 687 nm, showing measurements and calculated results with and without considering particle interaction.

Since the polydisperse HSPY model is a good approximation for modeling particle interactions of colloidal suspensions at high volume fractions, we can incorporate this model into the expression of isotropic scattering coefficient (i.e., Eq. 5) to recover an unknown particle size distribution. In this work, we recovered the particle size distribution of latex samples by fitting FDPM-measured $\mu'_s$, at various volume fractions at a wavelength of 687 nm or 828 nm using nonlinear regression. FIG. 15 illustrates the FDPM-measured and fitted isotropic scattering coefficients using the polydisperse HSPY model as a function of volume fraction at wavelengths of 687 nm. For comparison, the dotted line represents the theoretical value of the isotropic scattering coefficient neglecting particle interactions (i.e., $S(q)=1$), as predicted by using Eq. 5. It can be seen that particle interactions significantly contribute to the FDPM-measured isotropic scattering coefficient at high volume fraction, leading to a large deviation of the measured scattering coefficient from prediction by Mie theory. Table 4 lists the recovered mean sizes and deviations from FDPM measurements at wavelengths of 687 nm and 828 nm, which agree well with the DLS results measured at dilute latex sample (~0.01% volume fraction). These inversion results demonstrate that the FDPM method with the polydisperse HSPY structure factor model accounting for dominant particle interactions can be successfully used for recovery of particle size distribution of interacting colloidal suspensions at high volume fractions.

TABLE 4

|  | Mean (nm) | size Deviation (nm) | Polydispersity (%) |
| --- | --- | --- | --- |
| FDPM results (687 nm) | 142.23 | 25.46 | 17.9 |
| FDPM results (828 nm) | 143.14 | 21.84 | 15.3 |

The ability to recover particle size distribution of colloidal suspensions at high volume fractions depends largely upon finding an appropriate model for considering effects of particle-particle interactions. Most of available particle sizing methods require empirical calibration when sizing at high volume fractions due to unavailable models for considering particle interactions. Here it is demonstrated that the FDPM technique is a useful tool for probing particle interactions in polydisperse, concentrated, multiple scattering colloidal suspensions. Compared with theoretical predictions, the polydisperse HSPY model is suitable for description of particle interactions and local microstructure of colloidal suspensions at high volume fractions. By incorporating the polydisperse HSPY model to account for particle interactions, particle size distribution from FDPM measurements at high volume fractions (5–40%) were determined. The results agree well with DLS measurement at low volume fractions (~0.01%). While the previous work demonstrated that the FDPM technique can be used for particle sizing of multiple-scattering yet non-interacting colloidal suspension (<5% volume fraction), this work extends FDPM techniques to characterize interacting suspensions at high volume fraction. Compared with other methods, the FDPM technique is most suitable for particle sizing of colloidal suspensions at high volume fractions, due to the fact that: (1) it is based upon first principles; (2) it considers the effects of both multiple scattering and particle interactions; and (3) it is self-calibrating, and no external calibration is required.

In the above discussion, the particle interactions that were considered were brought about by volume exclusion effects; that is, by the fact that no two particles can occupy the same volume. As a result of this restriction, the particles in suspension become "ordered" or structured and the structure factor, S, or the partial structure factors, $S_{ij}$, become less than one. For most systems, the primary order in a suspension is caused by the volume exclusion effect. However, other more subtle interactions which arise due to interparticle forces can further add to the "order" and structure. The first-principles models for computing S and $S_{ij}$ for neutron and x-ray scattering are available or are becoming available in the open literature. Interaction forces that arise owing to electrostatics, depletion forces, van der Waals forces, etc., impact the order and, therefore, the structure.

FDPM offers an opportunity to assess these interactions and the parameters that govern them. When a particle size is known or determined by an auxiliary method, the scattering within a dense suspension can be accurately measured with FDPM and used to assess the forces which exist in dense suspensions. In the following, we demonstrate the approach by probing the effective surface charge of a dense suspension of negatively charged polystyrene.

Figure 16:
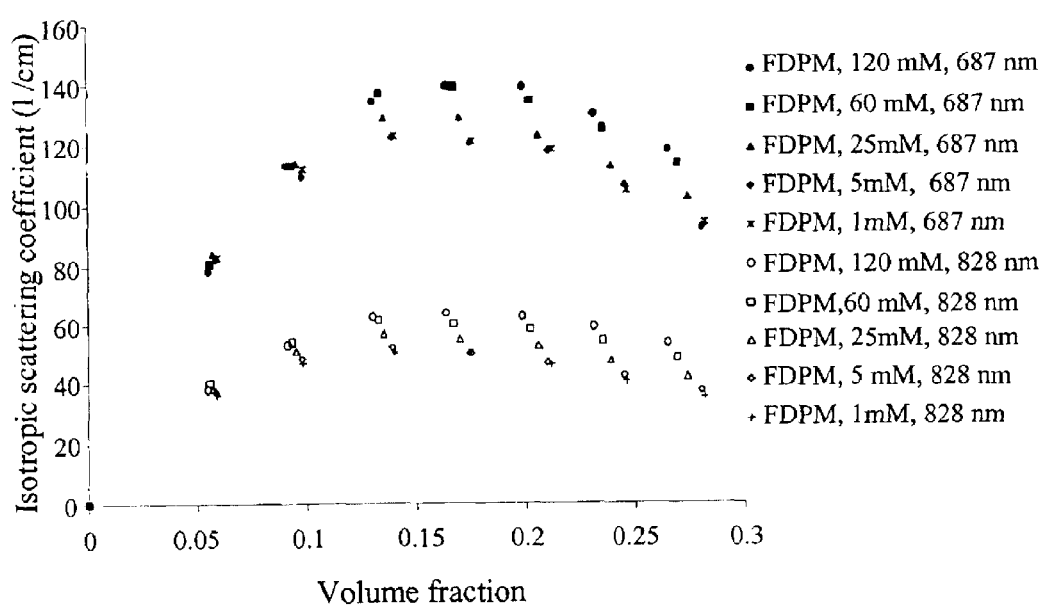
FIG. 16 shows the effect of salt content in a sample on measured scattering coefficients.

FIG. 16 illustrates the effect of salt concentration of a polystyrene sample on the isotropic scattering coefficient. At high volume fractions, scattering in the dialyzed sample is decreased because of greater interaction between the particles, which is caused by electrostatic repulsion and volume exclusion. When the salt concentration increases, this "screens" the electrostatic interaction and results in a reduction of order and consequently an increase in the scattering coefficient. The following discussion includes the characterization of dense suspensions under repulsive electrostatic interactions between particles. The discussion also applies to application of FDPM to assess changes in scattering due to electrostatic interactions, depletion forces, van der Waals force, steric forces and interaction parameters that relate to these forces. The interactions among colloidal particles decide the local structure, which can impact rheology, colloidal stability, and therefore the final performance of the industrial colloidal products. When characterizing colloidal systems using scattering techniques, such as x-ray and light scattering, the structure of the suspension has strong influence over scattering efficiency, especially at condensed cases.

The particle-particle interaction of charged particles can be considered as the addition of two parts: hard sphere interaction and electrostatic or other force interaction. Electrostatic interaction comes from the overlap of electrical double layers of particles while hard sphere interaction comes from volume exclusion effects or the simple fact that two particles cannot occupy the same volume. Upon evaluating a first principles model to account for the force, a structure factor or partial structure factor can be determined which is a function of the parameter governing the interparticle forces. In this example, the parameter impacting electrostatic interaction is the effective surface charge. The following outlines how the structure factor can be used to reflect these attractive and repulsive interactions from first principles.

Consider two unlike, interacting particles, i and j of diameter $x_i$ and $x_j$. Given a first principles model for the effective pair interaction potential, $U_{i,j}(r)$, between the two particles, the pairwise distribution function, $g_{i,j}$, and associated function, $h_{i,j}$, can be computed from the Boltzmann probability function in a dilute suspension:

$$g_{i,j}(r) = 1 + h_{i,j}(r) = \exp\left[\frac{-U_{i,j}(r)}{k_B T}\right] \qquad (30)$$

Here, the total correlation function, $h_{i,j}(r)$ is related to the sum of all direct correlations between i and j, denoted by $c_{i,j}(r)$ and all indirect effects on positional correlations between i and 1 mediated through particle 1. One relation that relates direct and indirect correlations of a dense ensemble is the Ornstein-Zernike (OZ) equation (Eq 31)

$$h_{i,j}(r) = c_{i,j}(r) + \sum_{l=1} \rho_l \int h_{i,l}(r') c_{l,j}(|r - r'|) dr' \qquad (31)$$

which requires a closure relating the total correlation, $h_{i,j}(r)$, to the direct correlations, $c_{i,j}(r)$, and the pair potential for solution. Closure relations such as the Percus-Yevick (P-Y), Roger-Young (RY), Hypernetted chain (HNC), and mean sphere approximation (MSA) must be employed to solve for the finclion $h_{i,j}(r)$. The three dimensional Fourier iransform of $h_{i,j}(r)$ is $H_{i,j}(q)$, where q (given by $q = 4\pi m/\lambda \sin(\theta/2)$) is the magnitude of the wavevector, q. Here, m is the refractive index of the medium and θ is the scattering angle. From the solution for $h_{i,j}(r)$ and therefore $H_{i,j}(q)$, the partial structure factor function, $S_{i,j}(q)$ can be subsequently defined as:

$$S_{i,j}(q) = \delta_{i,j} + \rho \sqrt{y_i y_j} H_{i,j}(q) \qquad (32)$$

where $y_i$ is the number fraction of component i and $\delta_{i,j}$ is the Kronecker delta function which equals unity when i=j.

In this example, we demonstrate how FDPM can be used to determine parameters which impact electrostatic interaction by considering a monodisperse suspension of known volume fraction and diameter. The interaction potential between charged monodisperse colloidal particles can be expressed as a hard sphere interaction with a Yukawa tail (HSY):

$$u(r) = \begin{cases} \infty & r < \sigma \\ e^2 z^2 <\sigma> \exp(-\kappa(r-\sigma))/(4\pi\varepsilon\varepsilon_0 r) & r > \sigma \end{cases} \qquad (33)$$

where e is electron charge; $\in_0$ is the electric permittivity of vacuum; and $\in$ is the dielectric constant of the suspending medium. The parameter σ is the particle diameter; z is the effective particle surface charge; κ is the inverse Debye screening length (which changes with the salt concentration); and r is the center-to-center distance between two particles. The above HSY potential model, also termed as the one-component model (OCM), does not conserve neutrality. In it, the charged particles are modeled as macro ions immersed in a neutral background but surrounded by the screened electric double layer of thickness $\kappa^{-1}$, which decreases with increasing solvent ionic strength. The charged particles repulsively interact through volume exclusion and double layer overlapping. The solution of the O-Z equation using MSA approximation with HSY potential is possible, as shown by Ginoza and Yasutomi and others [Herrera, J. N.; Cummings, P. T.; Ruiz-Estrada, H. R. "Static structure factor for simple liquid metals," Mol. Phys. 1999, 5, 835–847; Ginoza, M.; Yasutomi, M. "Analytical model of the static structure factor of a colloidal dispersion: interaction polydispersity effect," Mol. Phys. 1998, 93(3), 399–404.; Ginoza, M.; Yasutomi, M. "Analytical structure factors for colloidal fluids with size and interaction polydispersities," Phys. Rev. E, 1998, 58(3), 3329–3333.] An analytical and unique solution for the structure factor for monodisperse suspensions and the analytical partial structure factors for a polydisperse Yukawa mixture have been developed by Ginoza, M.; Yasutomi, M. "Analytical model of the static structure factor of a colloidal dispersion: interaction polydispersity effect," Mol. Phys. 1998, 93(3), 399–404; Ginoza, M.; Yasutomi, M. "Analytical structure factors for colloidal fluids with size and interaction polydispersities," Phys. Rev. E, 1998, 58(3), 3329–3333.

For polystyrene latex particles, the surface charge, z, corresponds to surface ionizable functional groups and cannot completely describe the effective electrostatic interactions when counter ion association occurs. Nonetheless, the effective surface charge, z, is typically used to compute the interaction between particles even though counter ion association may provide unmodeled mediation of the electrostatic interaction. In this contribution, the effective surface charge, z, for dense colloidal suspensions is obtained by regressing experimental values of isotropic scattering coefficients at varying volume fractions to predictions made using Mie theory and Herrera's solutions for MSA-HSY interactions.

From the FDPM measured isotropic scattering data presented in FIG. 16, the effective surface charge can be determined as illustrated in Table 5. This work shows that as the salt concentration or the "screening" changes, the effective charge by which the particles experience electrostatic interaction changes.

TABLE 5

| Ionic strength, NaCl equivalents | 120 mM | 60 mM | 25 mM | 5 mM | 1 mM |
| --- | --- | --- | --- | --- | --- |
| Debye screening Length (nm) | 0.88 | 1.24 | 1.93 | 4.31 | 9.63 |
| Effective Charge MSA-HSY | | | | | |
| 687 nm | 1.9 | 1240 | 836 | 404 | 137 |
| 828 nm | 0 | 1005 | 1137 | 489 | 184 |

Figure 17:
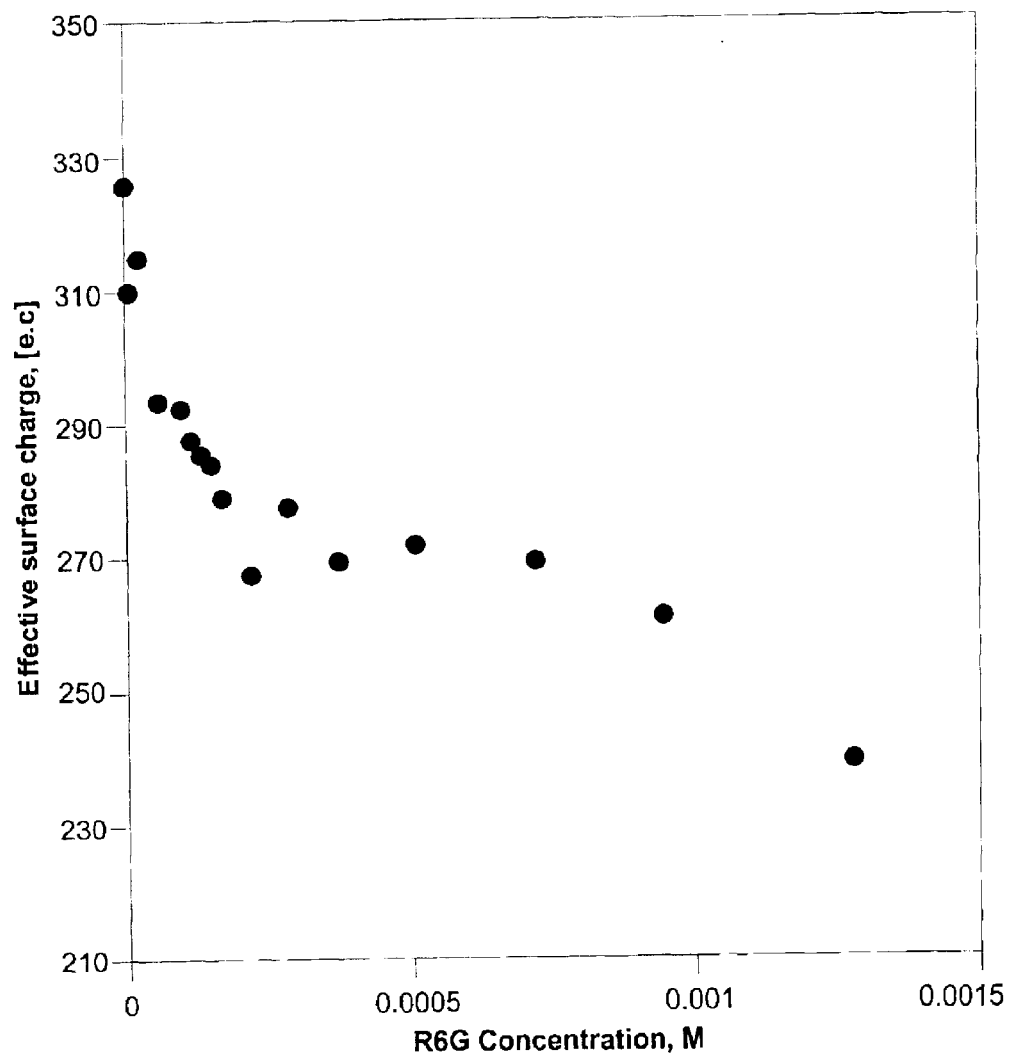
FIG. 17 shows the computation of an effective charge on particles as cationic surfactant is adsorbed onto negatively charged particles in suspension.

To demonstrate that the approach was sensitively evaluating electrostatic interactions, the salt concentration was held constant in the dense suspension, but cationic surfactant (Rhodamine 6G), which adsorbed onto the surface of negatively charged polystyrene, was added in small amounts. From the scattering data, the effective surface charge determined from the scattering data decreased as one would expect, further demonstrating that FDPM measurements in conjunction with a first principles model for particle interaction can be used to probe the nature of interactions in dense suspensions. FIG. 17 illustrates the results of effective surface charge of the particles as a finction of cationic concentration in the dense suspension. The effective surface charge was determined from FDPM measurements of a 143 nm diameter polystyrene suspension of 18.9% by volume solids with 5 mM NaCl equivalents. As the concentration of cationic Rhodamine 6G surfactant increased, the scattering increased and the effective surface charge was obtained by regressing FDPM data for predictions using the MSA-HSY model with effective charge as the only variable. For systems in which the particle size is known from another technique, FDPM measurements can be used to determine the nature of particle interactions.

It should be understood that the apparatus and methods described herein may also be applied to aerosols at concentrations in which multiple scattering from suspended particles may occur.

A partial list of the symbols used herein follows:

| | |
| --- | --- |
| $f(x)$ | particle size distribution |
| $F$ | scattering form factor of particles |
| $F_{i,j}$ | scattering form factor for particles i and j |
| $k$ | magnitude of wave vector |
| $K(x, \lambda_i)$ | kernel function used in inversing non-linear integral equation |
| $m$ | refractive index of medium |
| $n$ | relative refractive index of particle to medium |
| $S(q)$ | static structure factor |
| $S_{i,j}$ | partial static structure factor for particles i and j |
| $q$ | magnitude of scattering vector |
| $x$ | particle diameter |
| $\chi^2$ | objective function used for minimization |
| $\lambda$ | wavelength in medium |
| $\theta$ | scattering angle |
| $\phi$ | volume fraction of solids in suspension |
| $\mu_a$ | absorption coefficient |
| $\mu'_s$ | isotropic scattering coefficient |

In the foregoing written description, the invention has been described with reference to specific embodiments. However, after reading this description one of ordinary skill in the art appreciates that various modifications and changes can be made without departing from the scope of the present invention as set forth in the claims below.

What we claim is:

1. A method for determining at least one of parameters describing a non-interacting suspension, the parameters consisting of a particle size distribution and a volume fraction, comprising:

measuring an experimental scattering coefficient at a selected number of wavelengths of a radiation passing through the suspension;

formulating an integral equation for a calculated scattering coefficient, the integral equation having an integrand including a product, p(x), of the particle size distribution and the volume fraction, a form factor and a structure factor;

expressing p(x) as a summation of B-spline functions;

calculating the form factor from Mie scattering theory;

calculating an inverse of the integral equation using least squares optimization to equate the experimental scattering coefficient and the calculated scattering coefficient, stabilizing the inverse using Tikhonov regularization having a regularization parameter and a non-negativity constraint on p(x) to determine a value of p(x);

separating particle size distribution and volume fraction by a normalized distribution constraint; and using input physical data and selected upper and lower bounds of particle size, calculating volume fraction.

2. The method of claim 1 further comprising, using the normalized distribution constraint, calculating the particle size distribution.

3. The method of claim 1 further comprising the step of using an L-curve to choose the regularization parameter.

4. The method of claim 1 wherein calculating the inverse is performed by active-set quadratic programming.

5. The method of claim 1 wherein the regularization parameter is second order.

6. The method of claim 1 wherein the suspension is an aerosol.

7. The method of claim 1 wherein the radiation is light.

8. A method for determining at least one of parameters describing an interacting suspension, the parameters consisting of a particle size distribution, a volume fraction and an interaction parameter, comprising:
   (a) measuring an experimental scattering coefficient at a selected number of wavelengths of radiation passing through the suspension;
   (b) formulating an integral equation for a calculated scattering coefficient, the integral equation having an integrand including a product, p(x), of the particle size distribution and the volume fraction, a form factor and a structure factor;
   (c) inputting an assumed or newly calculated value of particle size distribution and an assumed or newly calculated value of the interaction parameter;
   (d) expressing p(x) as a summation of B-spline functions;
   (e) calculating the form factor from Mie scattering theory and a particle interaction model;
   (f) calculating an inverse of the integral equation using least squares optimization to equate the experimental scattering coefficient and the calculated scattering coefficient, stabilizing the inverse using Tikhonov regularization having a regularization parameter and a non-negativity constraint on p(x) to determine a value of p(x);
   (g) separating particle size distribution and volume fraction by a normalized distribution constraint;
   (h) using input physical data and selected upper and lower bounds of particle size, calculating an updated value of volume fraction;
   (i) comparing a difference between the assumed or a newly calculated value of volume fraction with the updated value of volume fraction to determine if the difference is less than a first selected convergence error;
   (j) repeating steps (d) through (i) until the difference is less than the selected convergence error to determine an experimental value of volume fraction and, from p(x), an experimental value of the particle size distribution;
   (k) calculating an updated experimental value of the interaction parameter using the selected interaction model;
   (l) comparing a difference between the assumed or a newly calculated value of interaction parameter with the updated calculated value of interaction parameter to determine if the difference is less than a second convergence error; and
   (m) repeating steps (d) through (k) until the difference is less than the convergence error to determine an experimental value of the interaction parameter for the suspension.

9. The method of claim 8 wherein the interaction model includes the LMA approximation to the HSPY model.

10. The method of claim 8 wherein the interaction model includes the DA approximation to the HSPY model.

11. The method of claim 8 further comprising the step of using an L-curve to choose the regularization parameter.

12. The method of claim 8 wherein calculating the inverse is performed by active-set quadratic programming.

13. The method of claim 8 wherein the regularization parameter is second order.

14. A system for executing a computer program to calculate at least one of parameters describing a suspension, the parameters consisting of a particle size distribution and a volume fraction, comprising:
   a memory device for storing the computer program thereon;
   a processor, the processor adapted to
   receive a request from a device for calculation of at least one of the parameters, receive input data for physical constants, upper and lower bounds of particle size and an experimental isotropic scattering coefficient, and
   execute the computer program to calculate an inverse of an integral equation for a calculated scattering coefficient by using a least squares optimization to equate the experimental scattering coefficient and the calculated scattering coefficient to determine volume fraction and particle size distribution of the suspension, based on received input data; and
   forward the result of the calculation to an output device.

15. The system of claim 14 wherein the suspension is an aerosol.

16. A system for executing a computer program to calculate at least one of parameters describing a suspension, the parameters consisting of a particle size distribution, a volume fraction and an interaction parameter, comprising:
   a memory device for storing the computer program thereon;
   a processor, the processor adapted to
   receive a request from a device for calculation of at least one of the parameters, receive input data for physical constants, upper and lower bounds of particle size distribution, an experimental isotropic scattering coefficient and assumed values of volume fraction and interaction parameter,
   execute the computer program to calculate an inverse of an integral equation for a calculated scattering coefficient by using a least squares optimization to equate the experimental scattering coefficient and the calculated scattering coefficient using the assumed values of volume fraction and interaction parameter to determine initial values of volume fraction and particle size distribution of the suspension, based on the received input data, and
   compare assumed and initial values of volume fraction and interaction parameter to check for a convergence and repeat the calculation until the convergence is obtained; and
   forward the result of the calculation to an output device.

17. A method for measuring a parameter governing interparticle forces in a suspension, comprising:
   measuring an experimental scattering coefficient at a selected number of wavelengths of a radiation passing through the suspension;
   formulating an integral equation for a calculated scattering coefficient, the integral equation having an integrand including a particle size distribution, a volume fraction, a form factor and a structure factor;
   calculating the form factor from Mie scattering theory;
   formulating the structure factor as a function of a parameter governing an interparticle force;
   calculating an inverse of the integral equation using least squares optimization to equate the experimental scattering coefficient and the calculated scattering coefficient; and
   calculating the structure factor and thereby the parameter governing the interparticle force.

18. The method of claim 17 wherein the interparticle force is electrostatic.

19. The method of claim 17 wherein the parameter is effective surface charge.

* * * * *